(12) United States Patent
Isaacson et al.

(10) Patent No.: US 11,648,385 B2
(45) Date of Patent: May 16, 2023

(54) AUTOMATIC DISINFECTION OF A VASCULAR ACCESS DEVICE CONNECTOR

(71) Applicant: Becton, Dickinson and Company, Franklin Lakes, NJ (US)

(72) Inventors: S. Ray Isaacson, Layton, UT (US); George Mansour, Diamond Bar, CA (US); Brian Tanner, Layton, UT (US); He Bai, Sandy, UT (US); Sophia Lijun Wang, Draper, UT (US); Shaun Staley, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 331 days.

(21) Appl. No.: 16/878,264

(22) Filed: May 19, 2020

(65) Prior Publication Data
US 2020/0376254 A1    Dec. 3, 2020

Related U.S. Application Data

(60) Provisional application No. 62/854,742, filed on May 30, 2019.

(51) Int. Cl.
*A61L 2/232* (2006.01)
*A61L 2/26* (2006.01)
(Continued)

(52) U.S. Cl.
CPC ......... *A61M 39/162* (2013.01); *A61L 2/232* (2013.01); *A61L 2/26* (2013.01); *A61M 25/0606* (2013.01); *A61M 25/0693* (2013.01); *A61M 39/165* (2013.01); *A61M 39/20* (2013.01); *A61M 39/26* (2013.01); *A61L 2202/17* (2013.01); *A61L 2202/24* (2013.01); *A61M 2025/0019* (2013.01)

(58) Field of Classification Search
None
See application file for complete search history.

(56) References Cited

U.S. PATENT DOCUMENTS

| 4,334,551 A | 6/1982 | Pfister |
| 4,442,133 A | 4/1984 | Greco et al. |

(Continued)

FOREIGN PATENT DOCUMENTS

| WO | 2006/062912 | 6/2006 |
| WO | 2011/064738 | 6/2011 |

*Primary Examiner* — Levon J Shahinian
(74) *Attorney, Agent, or Firm* — Kirton McConkie; Whitney Blair; Kevin Stinger

(57) ABSTRACT

A device to couple a vascular access device to a medical device may include a body, a spring, and a housing. The body may include a distal end, a proximal end, and a lumen extending through the distal end and the proximal end. The proximal end of the body may include a connector. The housing may be coupled to a proximal end of the spring and may enclose the connector. A distal end of the spring may be coupled to the body. The housing may include a flap, which may include an antimicrobial compound. When the housing is disposed in a proximal position, the flap may cover the connector, the antimicrobial compound may contact the connector, and the spring may be uncompressed. In response to movement of the housing from the proximal position to a distal position, the spring may be compressed and the flap may open.

16 Claims, 22 Drawing Sheets

(51) Int. Cl.
*A61M 25/06* (2006.01)
*A61M 39/16* (2006.01)
*A61M 39/20* (2006.01)
*A61M 39/26* (2006.01)
*A61M 25/00* (2006.01)

(56) References Cited

U.S. PATENT DOCUMENTS

| | | |
|---|---|---|
| 4,678,660 A | 7/1987 | McGary et al. |
| 4,713,402 A | 12/1987 | Solomon |
| 5,013,306 A | 5/1991 | Solomon et al. |
| 5,322,659 A | 6/1994 | Walder et al. |
| 6,261,271 B1 | 7/2001 | Solomon et al. |
| 8,066,670 B2 | 11/2011 | Cluff et al. |
| 8,691,887 B2 | 4/2014 | Ou-Yang |
| 8,754,020 B2 | 6/2014 | Ou-Yang |
| 2010/0137472 A1* | 6/2010 | Ou-Yang .............. C09D 5/1668 523/122 |
| 2018/0140819 A1 | 5/2018 | Yang |
| 2019/0381306 A1 | 12/2019 | Gish et al. |

* cited by examiner

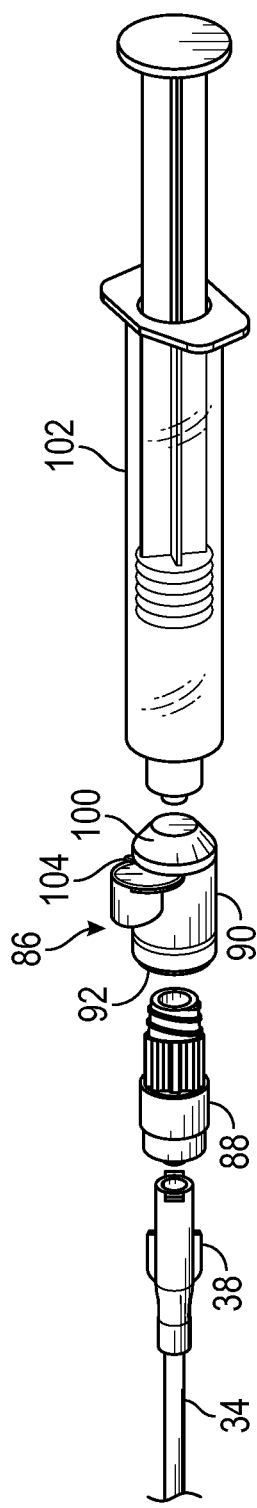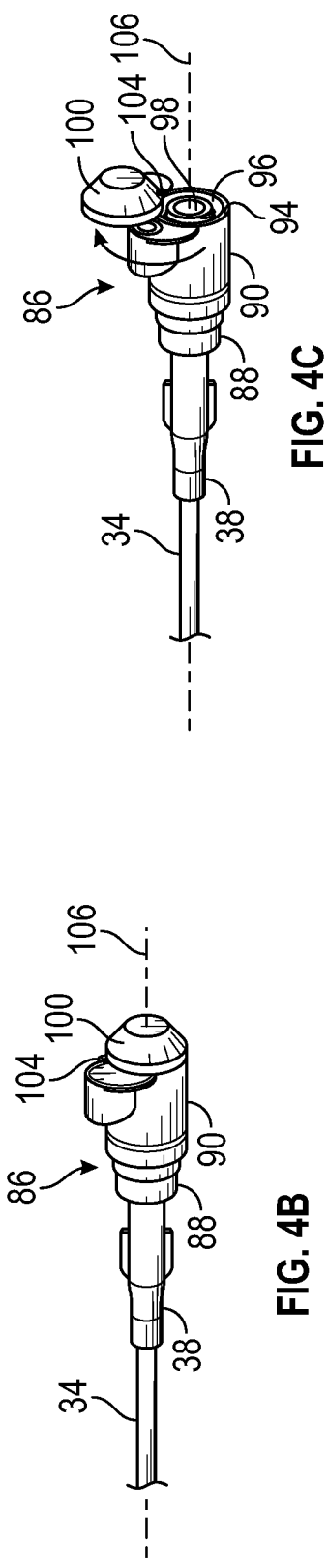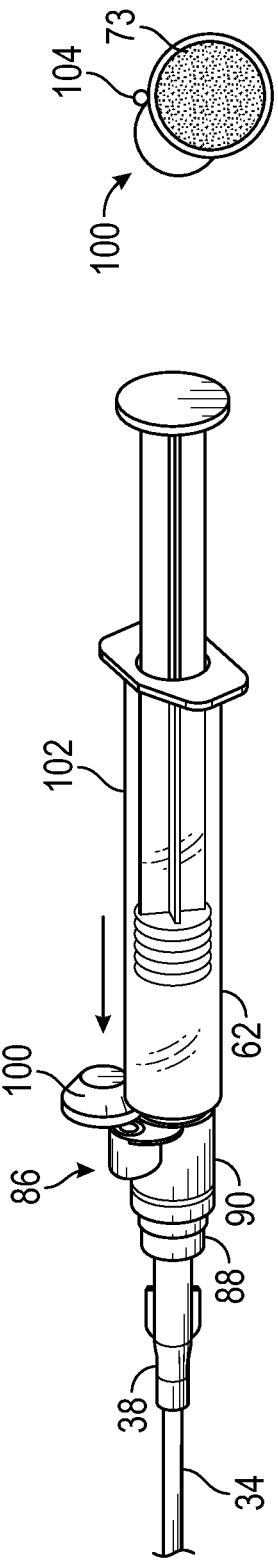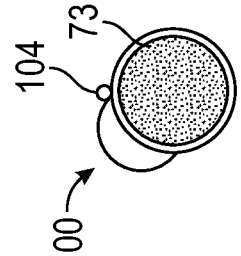

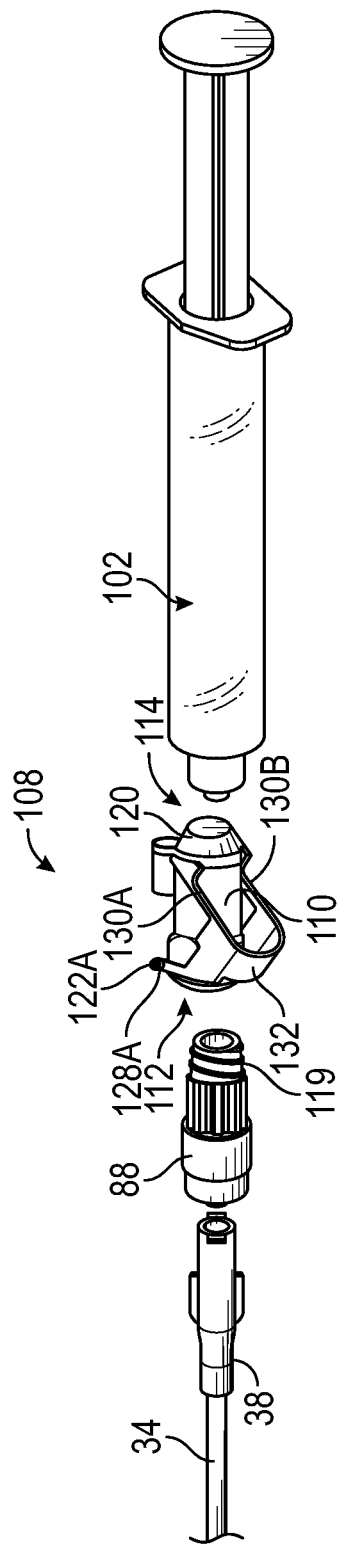
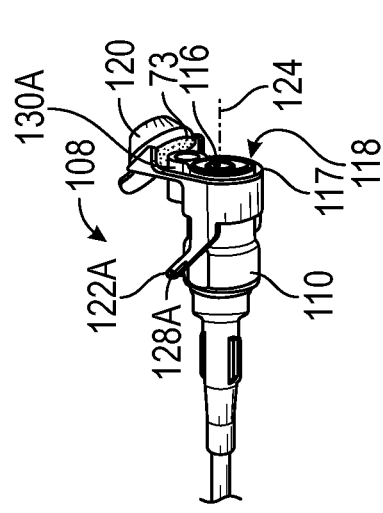
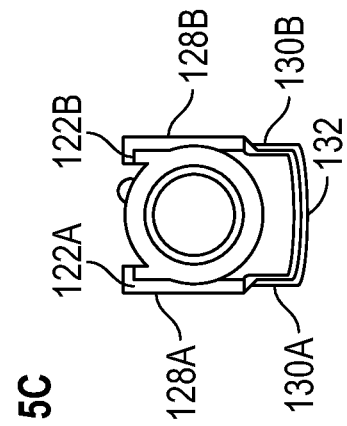
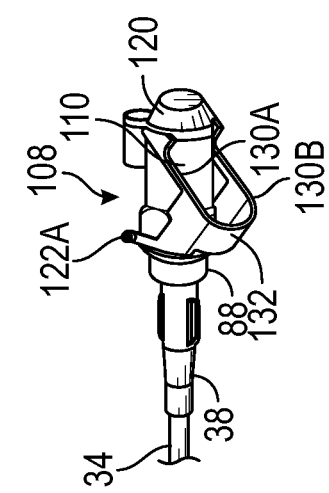
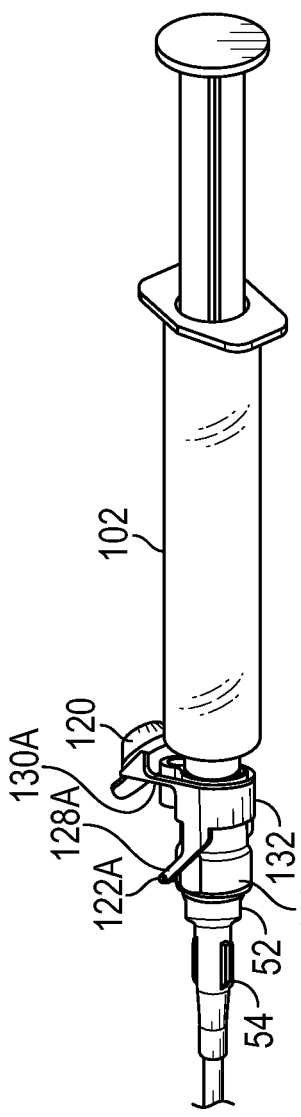

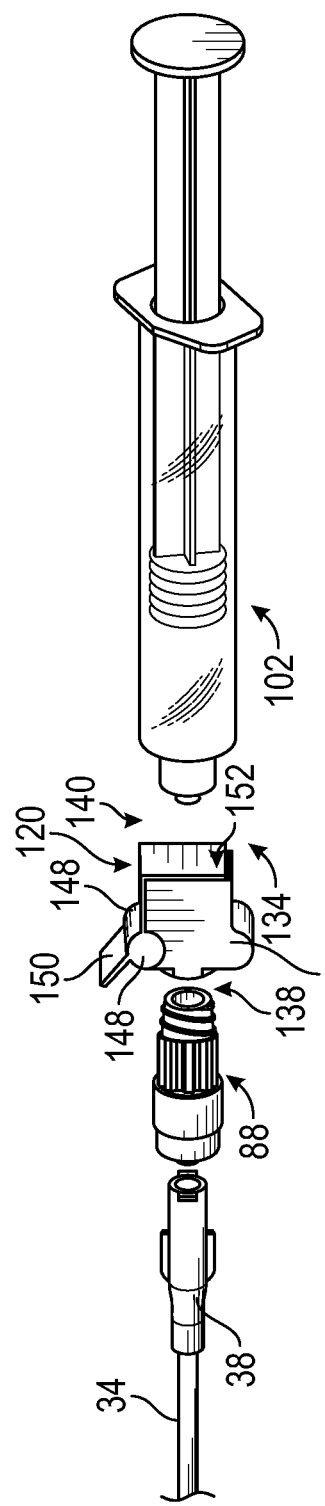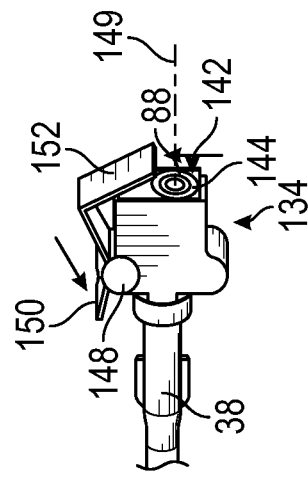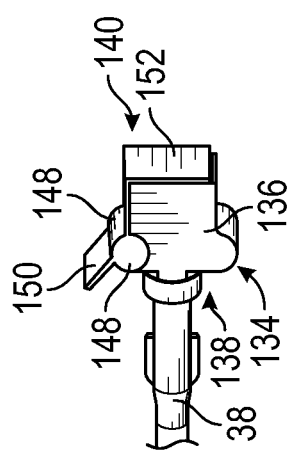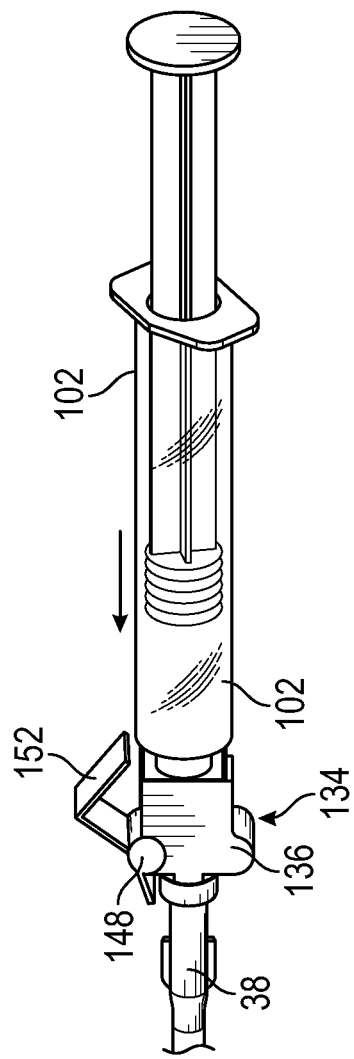

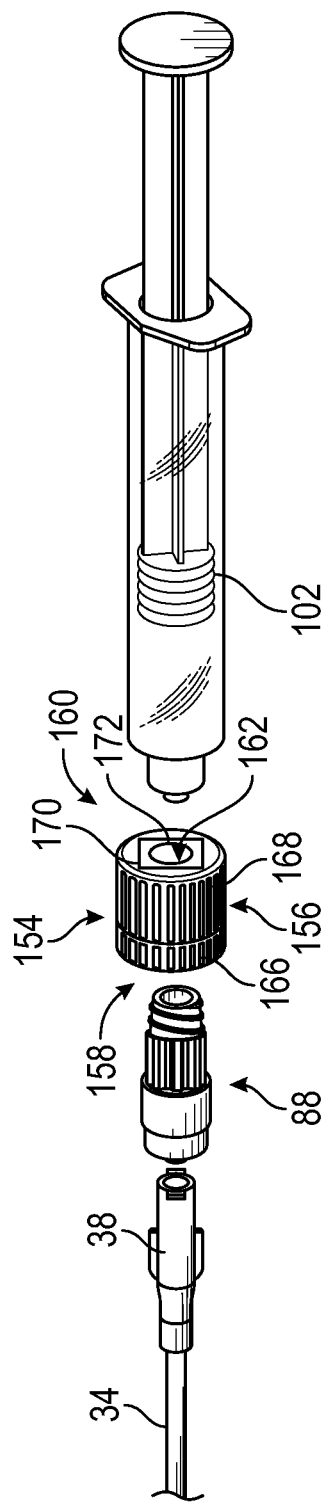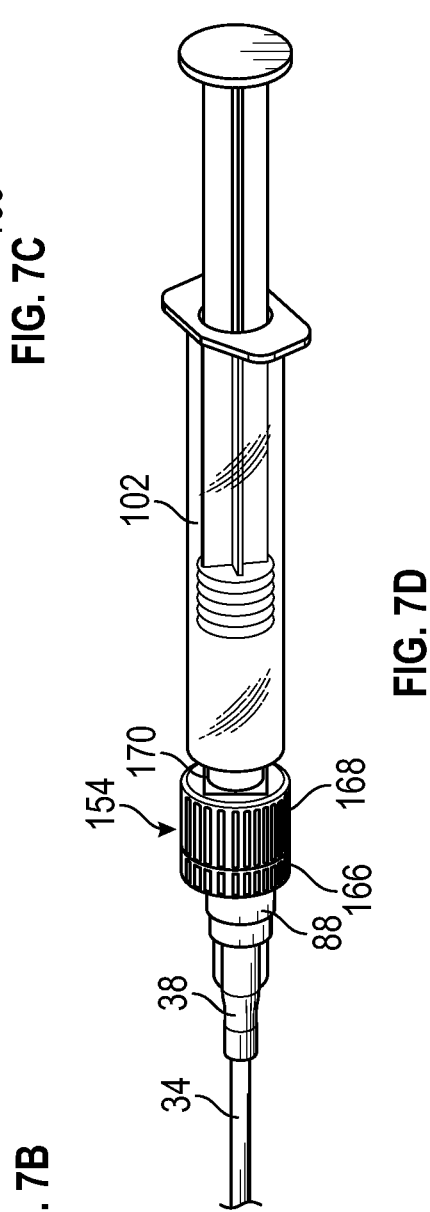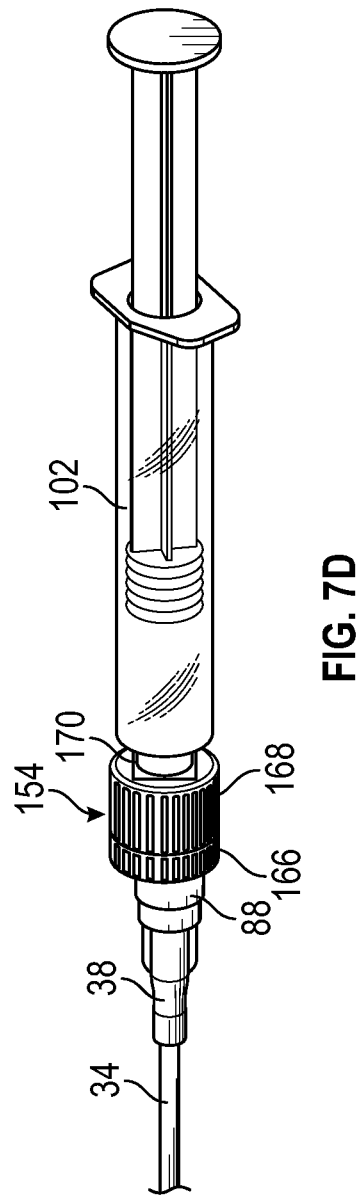

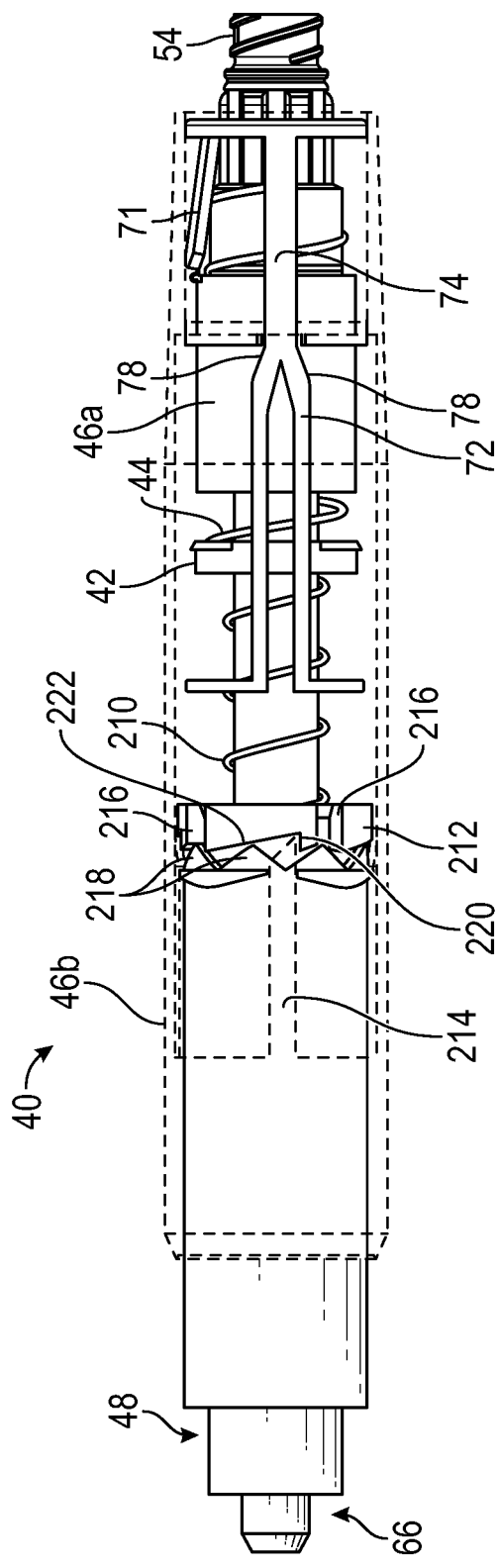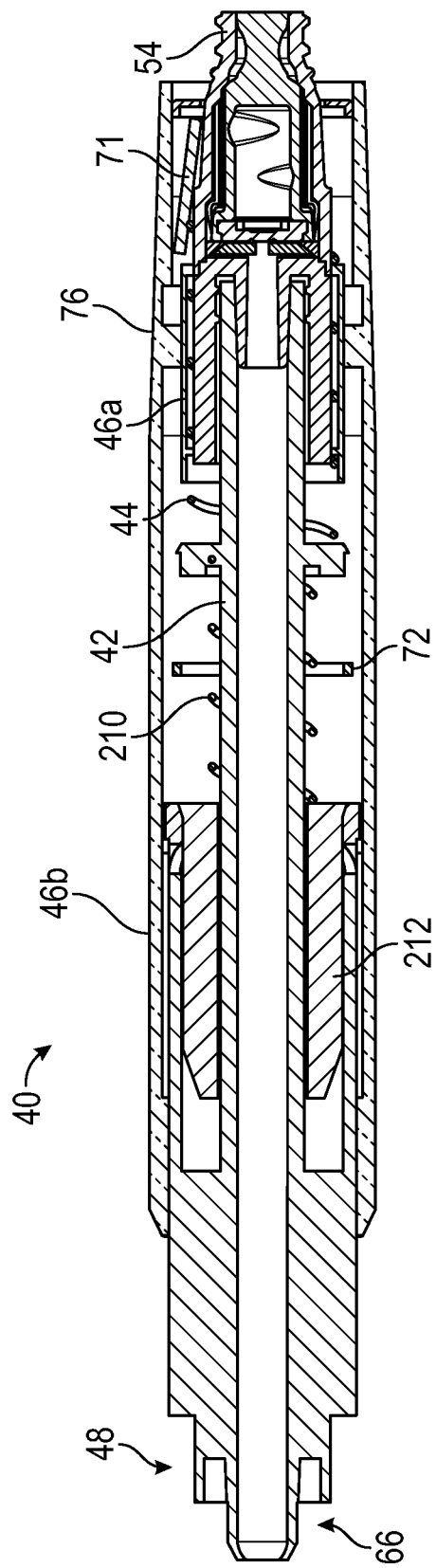
FIG. 9D
FIG. 9E

AUTOMATIC DISINFECTION OF A VASCULAR ACCESS DEVICE CONNECTOR

RELATED APPLICATIONS

This application claims the benefit of U.S. Provisional Patent Application No. 62/854,742, filed May 30, 2019, and entitled AUTOMATIC DISINFECTION OF A VASCULAR ACCESS DEVICE CONNECTOR which is incorporated herein in its entirety.

BACKGROUND

Intravenous catheters are commonly used for a variety of infusion therapies. For example, intravenous catheters may be used for infusing fluids, such as normal saline solution, various medicaments, and total parenteral nutrition, into a patient. Intravenous catheters may also be used for withdrawing blood from the patient.

Common types of intravenous catheter are peripheral IV catheters ("PIVCs"), peripherally inserted central catheters ("PICCs"), and midline catheters. Intravenous catheters may include "over-the needle" catheters, which may be mounted over an introducer needle having a sharp distal tip. The sharp distal tip may be used to pierce skin and the vasculature of the patient. Insertion of the intravenous catheter into the vasculature may follow the piercing of the vasculature by the needle. The needle and the intravenous catheter are generally inserted at a shallow angle through the skin into the vasculature of the patient with a bevel of the needle facing away from the skin of the patient. Once placement of the needle within the vasculature has been confirmed, the clinician may temporarily occlude flow in the vasculature and withdraw the needle, leaving the intravenous catheter in place for future blood withdrawal and/or fluid infusion.

A needleless connector may be used to connect the intravenous catheter with a medical device for fluid administration or blood withdrawal. The medical device may include a transfusion bag, syringe, or the like. Oftentimes, during infusion therapy, a proximal end of the needleless connector is left exposed to non-sterile surfaces. When the proximal end of the needleless connector is exposed, it may be contaminated by the clinician, the patient, bedding, a table, floor surfaces, or any number of other contamination sources.

Exposed needleless connectors are potential sites for intraluminal microbial contamination, which may lead to catheter related blood stream infection ("CRBSI"). CRBSIs are an important cause of illness and excess medical costs, as approximately 250,000 CRBSIs occur in United States intensive care units each year. Despite guidelines to help reduce healthcare associated infections, CRBSIs continue to plague our healthcare system. Needleless connectors have been identified as a source of contamination to cause CRBSI during fluid administration.

Current standards recommend disinfection of needleless connectors via a vigorous mechanical scrub and drying time prior to each use and suggest use of passive disinfection caps. Adherence to needleless connector disinfection protocols varies across clinicians and is further complicated by different manufacturers requiring different length of scrub and dry time, often resulting in incomplete disinfection of the needleless connector and increasing a risk of bloodstream infection. Use of passive disinfection caps is not ubiquitous at this time, often due to hospital policy, variability in clinician adherence to cap usage protocol, and the increased clinician time to find and place the disinfection caps.

The subject matter claimed herein is not limited to embodiments that solve any disadvantages or that operate only in environments such as those described above. Rather, this background is only provided to illustrate one example technology area where some implementations described herein may be practiced.

SUMMARY

In some embodiments, a device to couple a vascular access device to a medical device may include a body, a spring, and a housing. In some embodiments, the body may include a distal end, a proximal end, and a lumen extending through the distal end and the proximal end. In some embodiments, the proximal end of the body may include a connector, which may include a needleless connector or another connector. In some embodiments, the distal end of the body may include a luer connector or another suitable connector coupled to a vascular access device.

In some embodiments, the housing may be coupled to a proximal end of the spring and may enclose the connector. In some embodiments, a distal end of the spring may be coupled to the body. In some embodiments, the housing may include a flap, which may include an antimicrobial compound. In some embodiments, when the housing is disposed in a proximal position, the flap may cover the connector, the antimicrobial compound may contact the connector, and the spring may be uncompressed. In some embodiments, in response to movement of the housing from the proximal position to a distal position, the spring may be compressed and the flap may open.

In some embodiments, the device may include a support structure, which may include one or more elongated guides. In some embodiments, the housing may include one or more flanges. In some embodiments, in response to movement of the housing from the proximal position to the distal position, the flanges may be configured to move along the elongated guides in a distal direction.

In some embodiments, the elongated guide may include one or more stops. In some embodiments, the flanges may be configured to move along the guides in the distal direction when the flanges are proximal to and spaced apart from the stops. In some embodiments, in response to movement of the housing in the distal direction and the flange contacting the stop, the housing and the support structure may be configured to move together in the distal direction.

In some embodiments, a proximal end of the support structure may include an opening. In some embodiments, a diameter of the opening may be less than a diameter of the flap, which may prevent the flap from fully opening when the housing is disposed in the proximal position.

In some embodiments, a device to disinfect a vascular access device connector may include an inner housing and an outer housing. In some embodiments, the inner housing may include a proximal opening and may be configured to receive the vascular access device connector. In some embodiments, the outer housing may be moveable with respect to the inner housing between a proximal position and a distal position. In some embodiments, the outer housing may include a set of teeth.

In some embodiments, the device may include a rachet wheel, which may include an inner set of teeth and an outer set of teeth. In some embodiments, a first mandrel may extend through the rachet wheel and may include a pawl. In some embodiments, a second mandrel may be disposed on an opposite side of the inner housing as the first mandrel.

In some embodiments, antimicrobial strip may be wrapped around the second mandrel and coupled to the first mandrel. In some embodiments, the antimicrobial strip may extend over the proximal opening of the inner housing. In some embodiments, in response to movement of the outer housing between the proximal position and the distal position, the pawl may catch against the inner set of teeth, the set of teeth of the inner surface may successively engage the outer set of teeth, and the rachet wheel and the mandrel may rotate such that the antimicrobial strip moves across the proximal opening of the inner housing.

In some embodiments, in response to movement of the outer housing between the proximal position and the distal position, the antimicrobial strip may wrapped around the first mandrel and/or unwrapped from the second mandrel. In some embodiments, the antimicrobial strip may include multiple holes configured to allow a medical device to couple to the vascular access device connector for infusion or blood withdrawal.

In some embodiments, the outer housing may include a flap. In some embodiments, in response to movement of the outer housing between the proximal position and the distal position, the flap may be opened. In some embodiments, the outer housing may be configured to enclose the vascular access device connector.

In some embodiments, the device may include another rachet wheel. In some embodiments, the first mandrel may extend through the other rachet wheel. In some embodiments, the antimicrobial strip may be disposed between the rachet wheel and the other rachet wheel. In some embodiments, the device may include an arm extending through the mandrel. In some embodiments, the mandrel may be configured to rotate with respect to the arm. In some embodiments, the arm may be coupled to the inner housing.

The object and advantages of the embodiments will be realized and achieved at least by the elements, features, and combinations particularly pointed out in the claims. It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which:

FIG. 4A is an exploded view of another example catheter system, according to some embodiments;

FIG. 4B is an upper perspective view of an example housing of the catheter system of FIG. 4A, illustrating the housing in a closed position, according to some embodiments;

FIG. 4C is another upper perspective view of the housing of FIG. 4B, illustrating the housing in an open position, according to some embodiments;

FIG. 4D is another upper perspective view of the housing of FIG. 4B coupled to an example needleless connector, according to some embodiments;

FIG. 4E is a bottom view of an example cover, according to some embodiments;

FIG. 5A is an exploded view of another example catheter system, according to some embodiments;

FIG. 5B is an upper perspective view of an example housing of the catheter system of FIG. 5A, illustrating the housing in a closed position, according to some embodiments;

FIG. 5C is another upper perspective view of the housing of FIG. 5B, illustrating the housing in an open position, according to some embodiments;

FIG. 5D is another upper perspective view of the housing of FIG. 5B coupled to an example needleless connector, according to some embodiments;

FIG. 5E is a proximal end view of the housing of FIG. 5B, according to some embodiments;

FIG. 6A is an exploded view of another example catheter system, according to some embodiments;

FIG. 6B is an upper perspective view of an example housing of the catheter system of FIG. 6A, illustrating the housing in a closed position, according to some embodiments;

FIG. 6C is another upper perspective view of the housing of FIG. 6B, illustrating the housing in an open position, according to some embodiments;

FIG. 6D is another upper perspective view of the housing of FIG. 6B coupled to an example needleless connector, according to some embodiments;

FIG. 7A is an exploded view of another example catheter system, according to some embodiments;

FIG. 7B is an upper perspective view of an example housing of the catheter system of FIG. 7A, illustrating the housing in an open position, according to some embodiments;

FIG. 7C is another upper perspective view of the housing of FIG. 7B, illustrating the housing in a partially closed position, according to some embodiments;

FIG. 7D is another upper perspective view of the housing of FIG. 7B coupled to an example needleless connector, according to some embodiments;

FIG. 9D is a side view of the device of FIG. 2A, illustrating the device in the projected position, according to some embodiments;

FIG. 9E is a cross-sectional view of the device of FIG. 2A, illustrating the device in the projected position, according to some embodiments;

DESCRIPTION OF EMBODIMENTS

Figure 1:
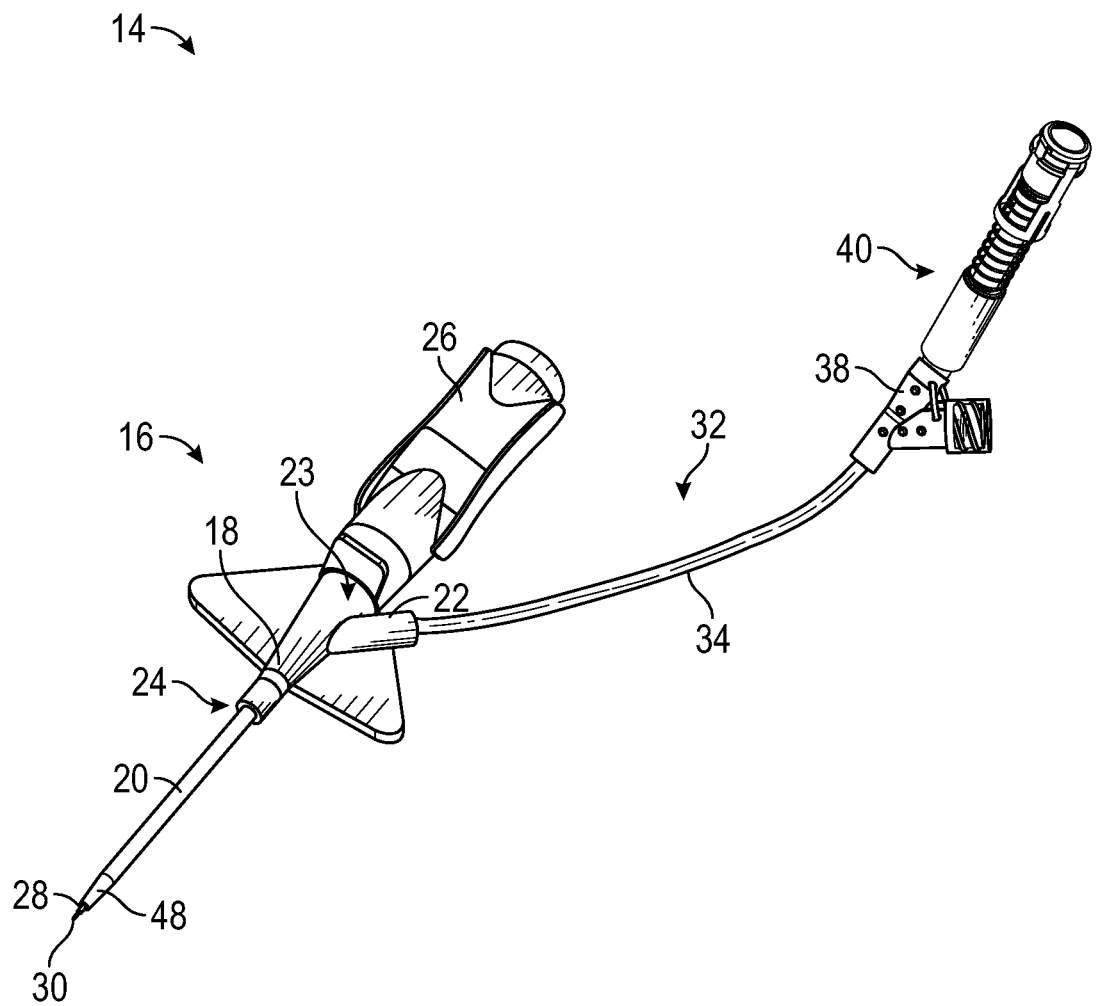
FIG. 1 is an upper perspective view of an example catheter system, according to some embodiments.

Referring now to FIG. 1, an example catheter system 14 is illustrated, according to some embodiments. In some embodiments, the catheter system 14 may include a catheter assembly 16. In some embodiments, the catheter assembly 16 may include a catheter adapter 18 and a catheter 20 extending distally from the catheter adapter 18. In some embodiments, the catheter adapter 18 may include a side port 22 in fluid communication with the lumen of the catheter adapter 18. In some embodiments, the catheter adapter 18 may include a proximal end 23, a distal end 24, and a lumen extending there between. In some embodiments, the catheter 20 may include a PIVC, a PICC, or a midline catheter.

In some embodiments, the catheter assembly 16 may be removably coupled to a needle assembly, which may include a needle hub 26 and an introducer needle 28. In some embodiments, the introducer needle 28 may include a sharp distal tip 30. In some embodiments, a proximal end of the introducer needle 28 may be secured within the needle hub 26. In some embodiments, the introducer needle 28 may extend through the catheter 20 when the catheter assembly 16 is in an insertion position ready for insertion into vasculature of a patient, as illustrated, for example, in FIG. 1. In some embodiments, in response to the introducer needle 28 being inserted into the vasculature of the patient, flashback of blood may flow through the sharp distal tip 30 of the introducer needle 28 and may be visible to a clinician between the introducer needle 28 and the catheter 20 and/or at another location within the catheter assembly 16.

In some embodiments, in response to confirmation via the blood flashback that the catheter 20 is positioned within vasculature of the patient, the needle assembly may be removed from the catheter assembly 16. In some embodiments, when the needle assembly is coupled to the catheter assembly 16, the introducer needle 28 of the needle assembly may extend through a septum disposed within the lumen of the catheter adapter 18.

In some embodiments, the catheter system 14 may include an extension set 32, which may include an extension tube 34 and/or a clamp (not illustrated). In some embodiments, a distal end of the extension tube 34 may be integrated with the catheter adapter 18. For example, the extension tube 34 may be integrated with the side port 22 of the catheter adapter 18. In some embodiments, the extension tube 34 may be removably coupled to the catheter adapter 18. In some embodiments, the clamp may selectively close off the extension tube 34 to prevent blood or another fluid from flowing through the extension tube 34.

In some embodiments, the extension set 32 may include an adapter 38 coupled to a proximal end of the extension tube 34. In some embodiments, the adapter 38 may include a Y-adapter or another suitable connector. In some embodiments, a device 40 may be coupled to the adapter 38. In some embodiments, the device 40 may be used to connect the catheter system 14 with a medical device for fluid administration or blood withdrawal. In some embodiments, the medical device may include a transfusion bag, syringe, or any other suitable medical device. In some embodiments, the device 40 may be configured to prevent contamination of a connector within the device 40, as will be explained in further detail.

In some embodiments, the device 40 may be used with the catheter system 14 of FIG. 1 or any other suitable catheter system. In some embodiments, the catheter system 14 may be integrated, having an integrated extension tube, such as, for example, the BD NEXIVA™ Closed IV Catheter System, the BD NEXIVA™ DIFFUSICS™ Closed IV Catheter System, the BD PEGASUS™ Safety Closed IV Catheter System, or other integrated catheter systems.

Referring now to FIG. 2A-3C, the device 40 may include one or more of the following: a body 42, a spring 44, and a housing 46. In some embodiments, the housing 46 may include an inner portion 46a, which may be coupled to an outer portion 46b. The outer portion is removed in FIGS.

Figure 3A:
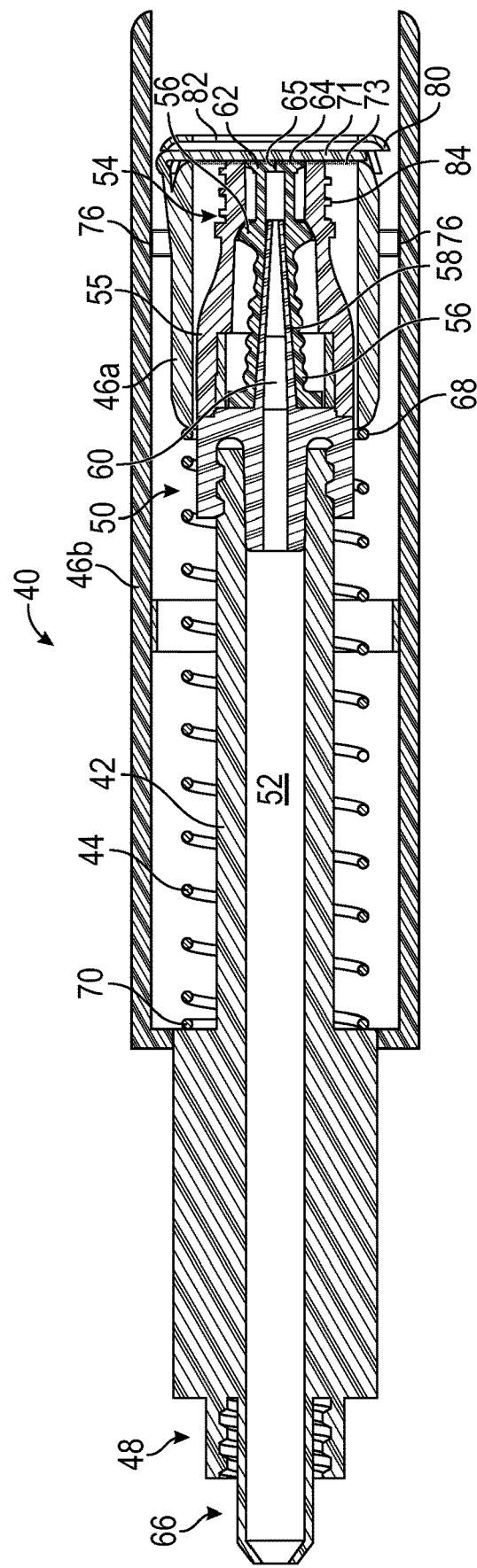
FIG. 3A is a cross-sectional view of the device of FIG. 2A, illustrating the housing disposed in the proximal position and including an outer portion, according to some embodiments.
Figure 3B:
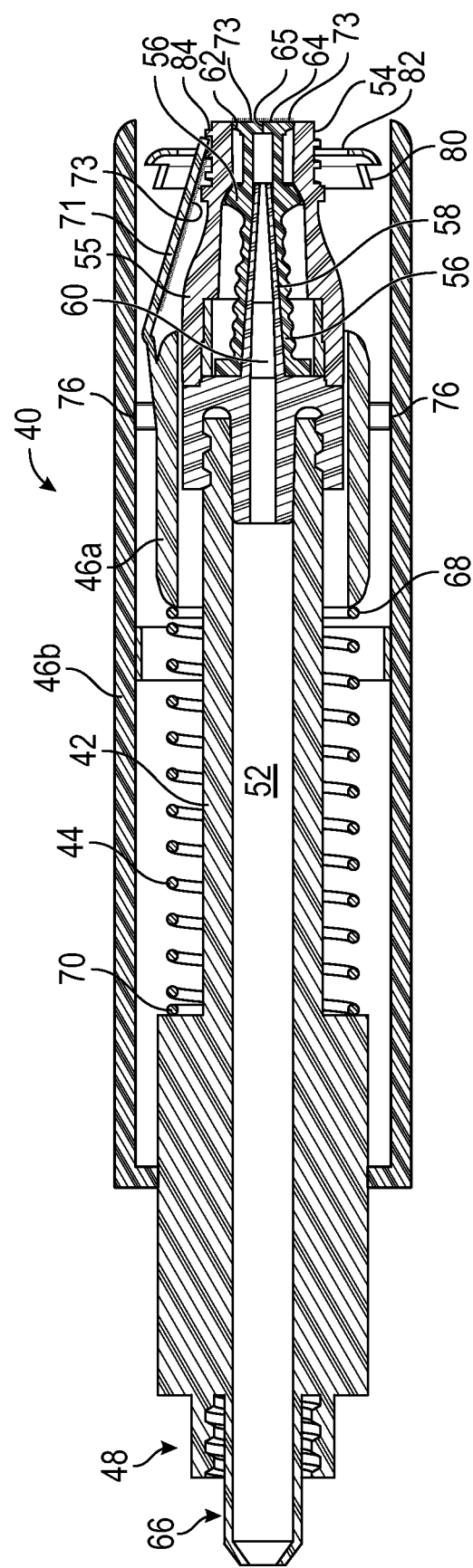
FIG. 3B is a cross-sectional view of the device of FIG. 2B, illustrating the housing disposed in the first distal position, according to some embodiments.
Figure 3C:
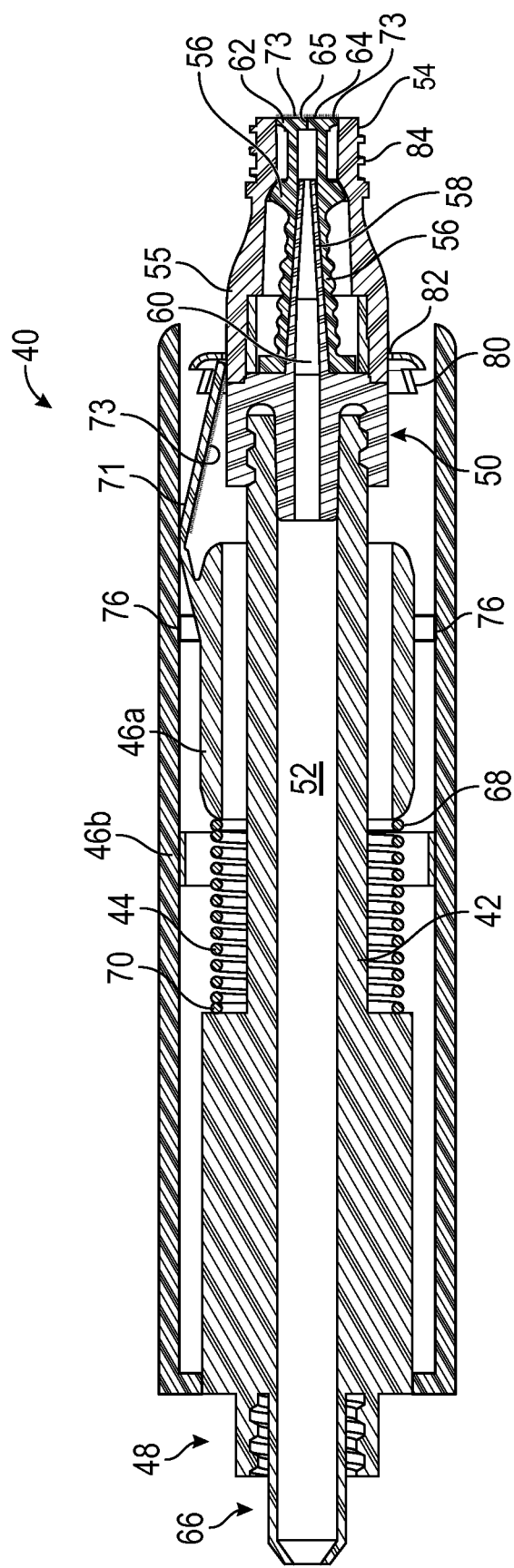
FIG. 3C is a cross-sectional view of the device of FIG. 2C, illustrating the housing disposed in the second distal position, according to some embodiments.
Figure 8C:
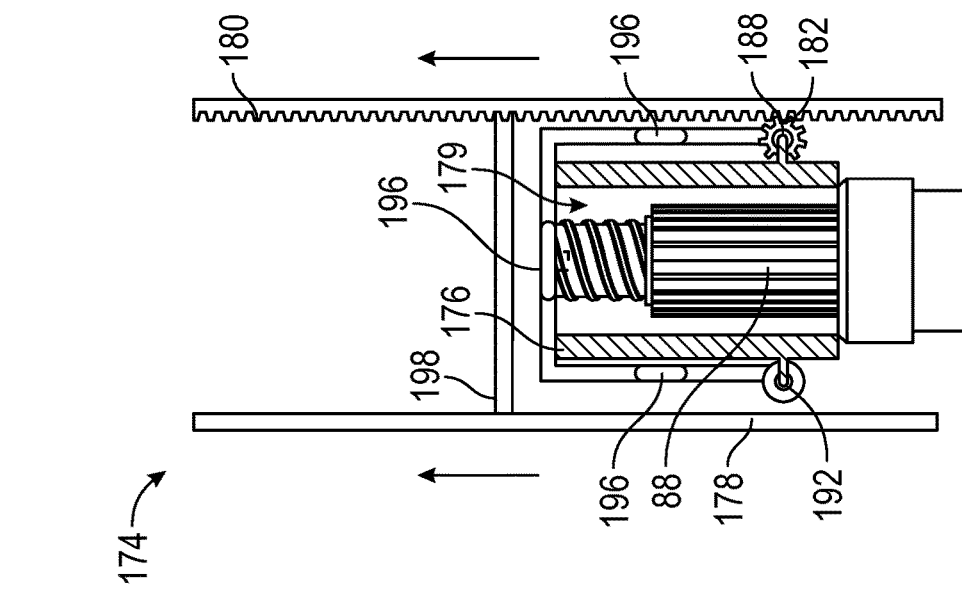
FIG. 8C is another partial cutaway view of the device of FIG. 8A, illustrating the outer housing moved to back to the proximal position, according to some embodiments.
Figure 8B:
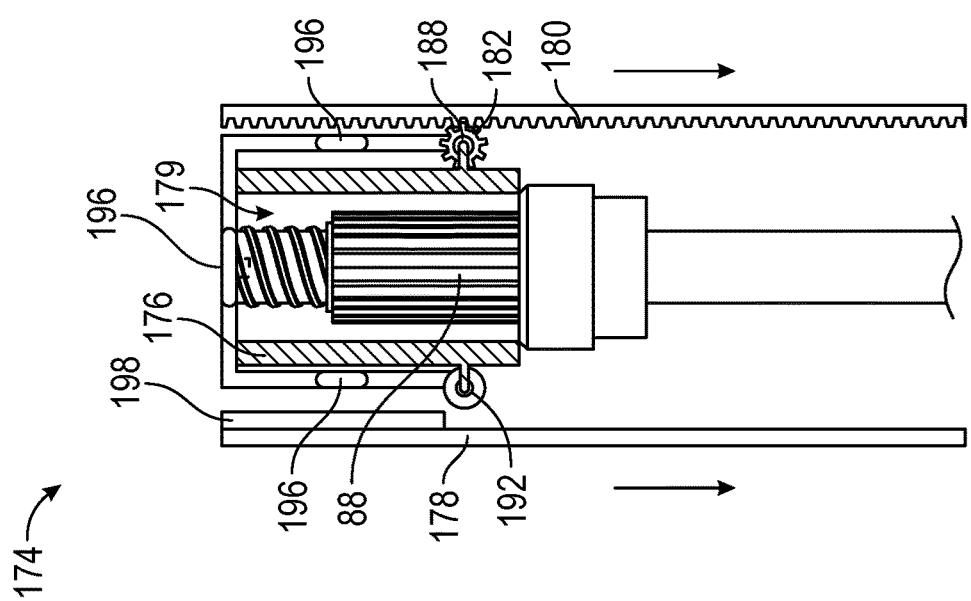
FIG. 8B is another partial cutaway view of the device of FIG. 8A, the outer housing moved to a distal position, according to some embodiments.
Figure 8A:
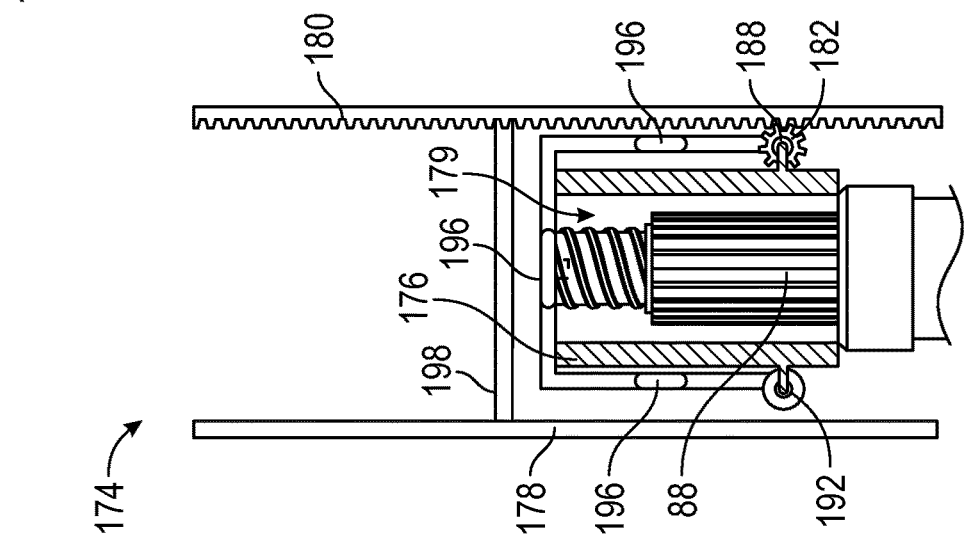
FIG. 8A is a partial cutaway view of an example device, illustrating an example outer housing disposed in a proximal position, according to some embodiments.
Figure 8D:
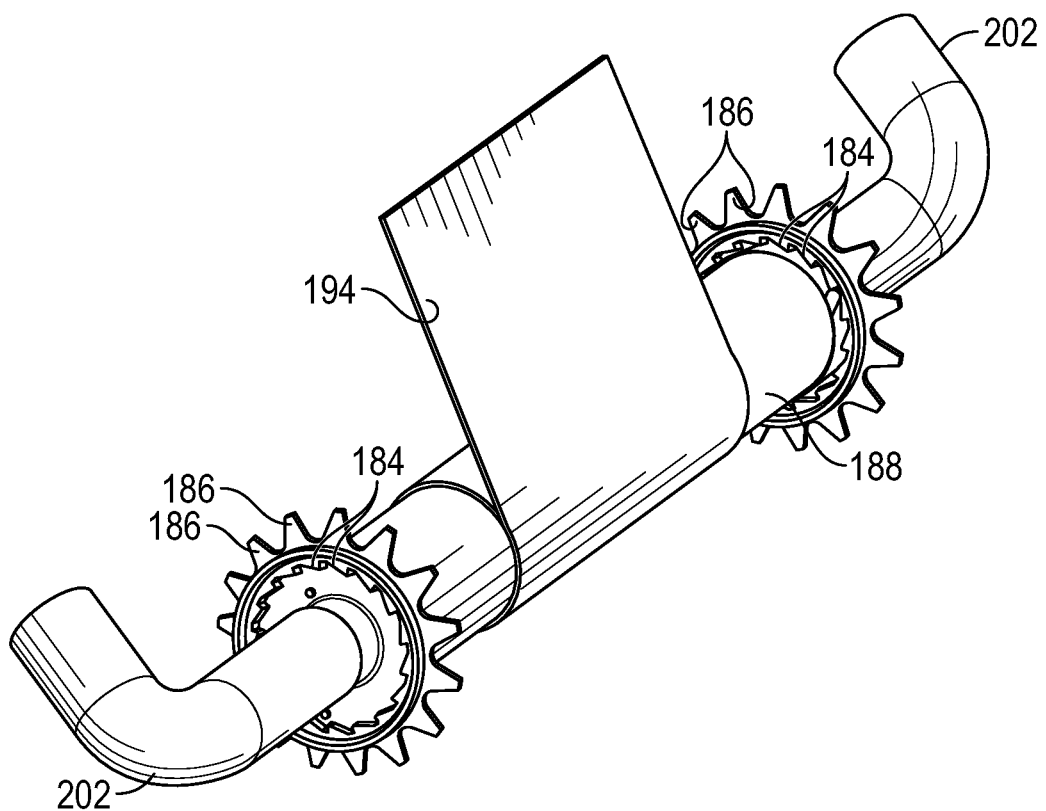
FIG. 8D is an upper perspective view of an example first mandrel of a rachet mechanism of the device of FIG. 8A, according to some embodiments.
Figure 8E:
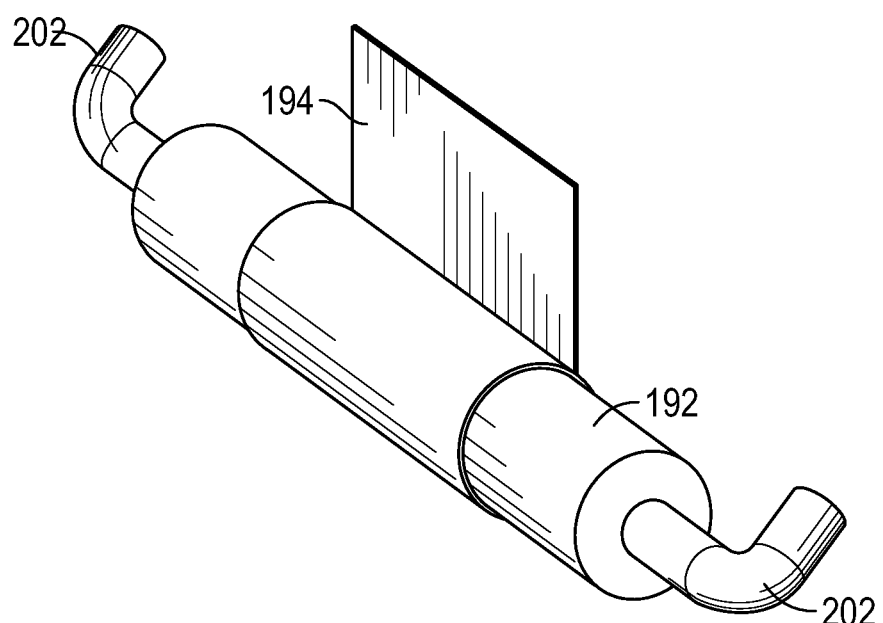
FIG. 8E is an upper perspective view of an example second mandrel of the device of FIG. 8A, according to some embodiments.
Figure 8F:
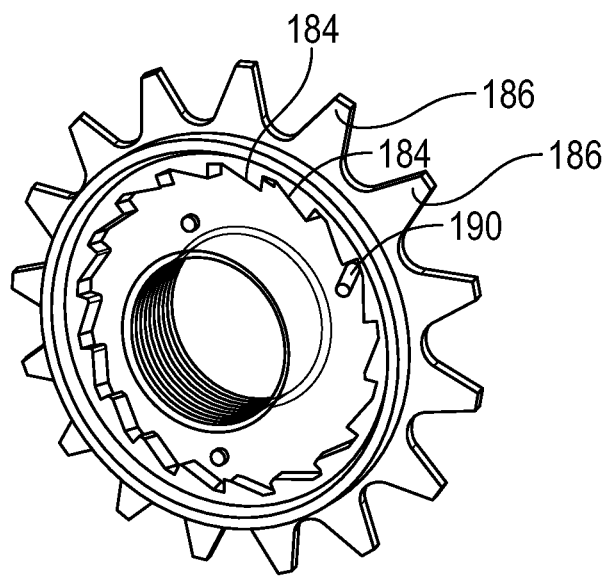
FIG. 8F is an upper perspective view of an example rachet wheel of FIG. 8D, illustrating an example pawl in a loose position, according to some embodiments.
Figure 8G:
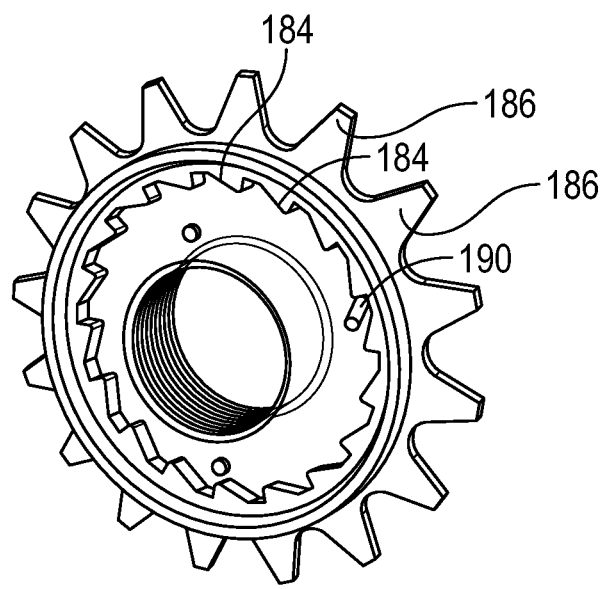
FIG. 8G is an upper perspective view of the rachet wheel of FIG. 8D, illustrating the in a catch position, according to some embodiments.

1-2C for illustration purposes, but is illustrated in FIGS. 3A-3C, according to some embodiments. In some embodiments, the body 42 may include a distal end 48, a proximal end 50, and a lumen 52 extending through the distal end 48 and the proximal end 50. In some embodiments, the proximal end 50 of the body 42 may include a connector 54. In some embodiments, the connector 54 may include a male or female Luer connector with a Luer-slip or Luer-Lock feature configured to couple the connector 54 to a medical device, such as, for example, the medical device 102 illustrated in FIGS. 4-7 or another suitable medical device.

In some embodiments, the connector 54 may include any suitable needleless connector. An example needleless connector may be described in U.S. Pat. No. 8,066,670, filed Nov. 5, 2007, entitled "VASCULAR ACCESS DEVICE SEPTUM VENTING," which is hereby incorporated by reference. In some embodiments, the needleless connector may include a SMARTSITE™ needle-free connector provided by Becton, Dickinson and Company.

In some embodiments, the connector 54 may include a body 55, a septum 56 disposed within the body 55, and an internal blunt cannula 58. In some embodiments, the septum 56 may include a split-septum. In some embodiments, the internal blunt cannula 58 may provide an internal fluid path 60 in fluid communication with the lumen 52 of the body 42. In some embodiments, an access luer of the medical device, such as an infusion device, may contact a proximal end 62 of the septum 56 and compress the septum 56, opening the internal fluid path 60. In some embodiments, when the access luer is removed, the septum 56 may return to cover the internal blunt cannula 58 and close the internal fluid path 60 once again. In some embodiments, the proximal end 62 may include a generally planar proximal surface 64, which may facilitate swabbing or scrubbing of the proximal end 62. In some embodiments, the septum 56 may include a slit 65.

In some embodiments, at least a portion of the connector 54 and the proximal end 50 may be monolithically formed as a single unit. In some embodiments, the connector 54 may be coupled to the proximal end 50 via a Luer connector, which may include a Luer-slip feature, a Luer-lock feature, (as illustrated, for example, in FIG. 3A), or another suitable connection.

In some embodiments, the distal end 48 of the body 42 may include a luer connector 66 or another suitable connector, which may be coupled to the catheter assembly 16. In some embodiments, the luer connector 66 may include a slip or thread male luer connector. In some embodiments, the distal end 48 of the body 42 may be coupled to the adapter 38, which may include a female luer adapter.

In some embodiments, the housing 46 may be movable with respect to the connector 54. In some embodiments, when the housing 46 is disposed in a proximal position, the connector 54 may be disposed within the housing 46. In some embodiments, in response to movement of the housing 46 from the proximal position to a distal position, the connector 54 may be disposed proximal to the housing 46. In some embodiments, the device 40 may not include the spring 44, and the housing 46 may be manually returned to the proximal position and/or moved to the distal position.

In some embodiments, the inner portion 46a may be coupled to the outer portion 46b at one or more of the flanges 76. In some embodiments, the inner portion 46a and the outer portion 46b may be integrally formed or monolithically formed as a single unit.

In some embodiments, the housing 46 may be coupled to a proximal end 68 of the spring 44 and may enclose the connector 54. In some embodiments, the connector 54 may be sealed within the housing 46. In some embodiments, a distal end 70 of the spring 44 may be coupled to the body 42. In some embodiments, the housing 46 may include a flap 71, which may include an antimicrobial compound 73. In some embodiments, the housing 46 may not include the flap 71.

As an example, one or more of the following: the body 55, the flap 71, and the housing 46, may be constructed of a thermoplastic material that may incorporate functional moieties, such as, for example, fluoro or silicone, which may tend to migrate onto a surface of the thermoplastic material. The functional moieties on the surface of the thermoplastic material may potentially reduce bacteria adhesion by creating a hydrophobic and lubricious environment. As another example, one or more of the following: the body 55, the housing 46, and the flap 71, may include the antimicrobial compound 73, which may be applied as an antimicrobial coating. As yet another example, the flap 71 may include a pad or cloth, which may include the antimicrobial compound 73.

In one particular embodiment, the antimicrobial agent used as the antimicrobial compound 73 included in the pad or the cloth of the flap 71 or in the antimicrobial coating may include chlorhexidine including chlorhexidine diacetate (CHA) and chlorhexidine gluconate (CHG). However, any other antimicrobial agent as widely reported in literature could also be used. Non-limiting examples of the antimicrobial coating and related application methods may be described in: U.S. Pat. No. 8,691,887, filed Jun. 2, 2009, entitled "ANTIMICROBIAL COATING COMPOSITIONS"; U.S. Pat. No. 8,754,020, filed Apr. 22, 2013, entitled "ANTIMICROBIAL LUBRICANT COMPOSITIONS"; U.S. Pat. No. 4,713,402, filed Aug. 30, 1985, entitled "PROCESS FOR PREPARING ANTITHROMBOGENIC/ANTIBIOTIC POLYMERIC PLASTIC MATERIALS" U.S. Pat. No. 4,442,133, filed Feb. 22, 1982, entitled "ANTIBIOTIC BONDING OF VASCULAR PROSTHESES AND OTHER IMPLANTS"; U.S. Pat. No. 4,678,660, filed Aug. 14, 1985, entitled "THERMOPLASTIC POLYURETHANE ANTICOAGULANT ALLOY COATING;" U.S. Pat. No. 5,013,306, filed Mar. 21, 1990, entitled "ANTI-INFECTIVE AND ANTITHROMBOGENIC MEDICAL ARTICLES AND METHOD FOR THEIR PREPARATION"; U.S. Pat. No. 6,261,271, filed Jan. 13, 1998, entitled "ANTI-INFECTIVE AND ANTITHROMBOGENIC MEDICAL ARTICLES AND METHOD FOR THEIR PREPARATION"; and U.S. Pat. No. 5,322,659, filed Sep. 21, 1990, entitled "METHOD FOR RENDERING A SUBSTRATE SURFACE ANTITHROMBOGENIC AND/ OR ANTI-INFECTIVE," each of which is incorporated herein by reference.

Figure 2A:
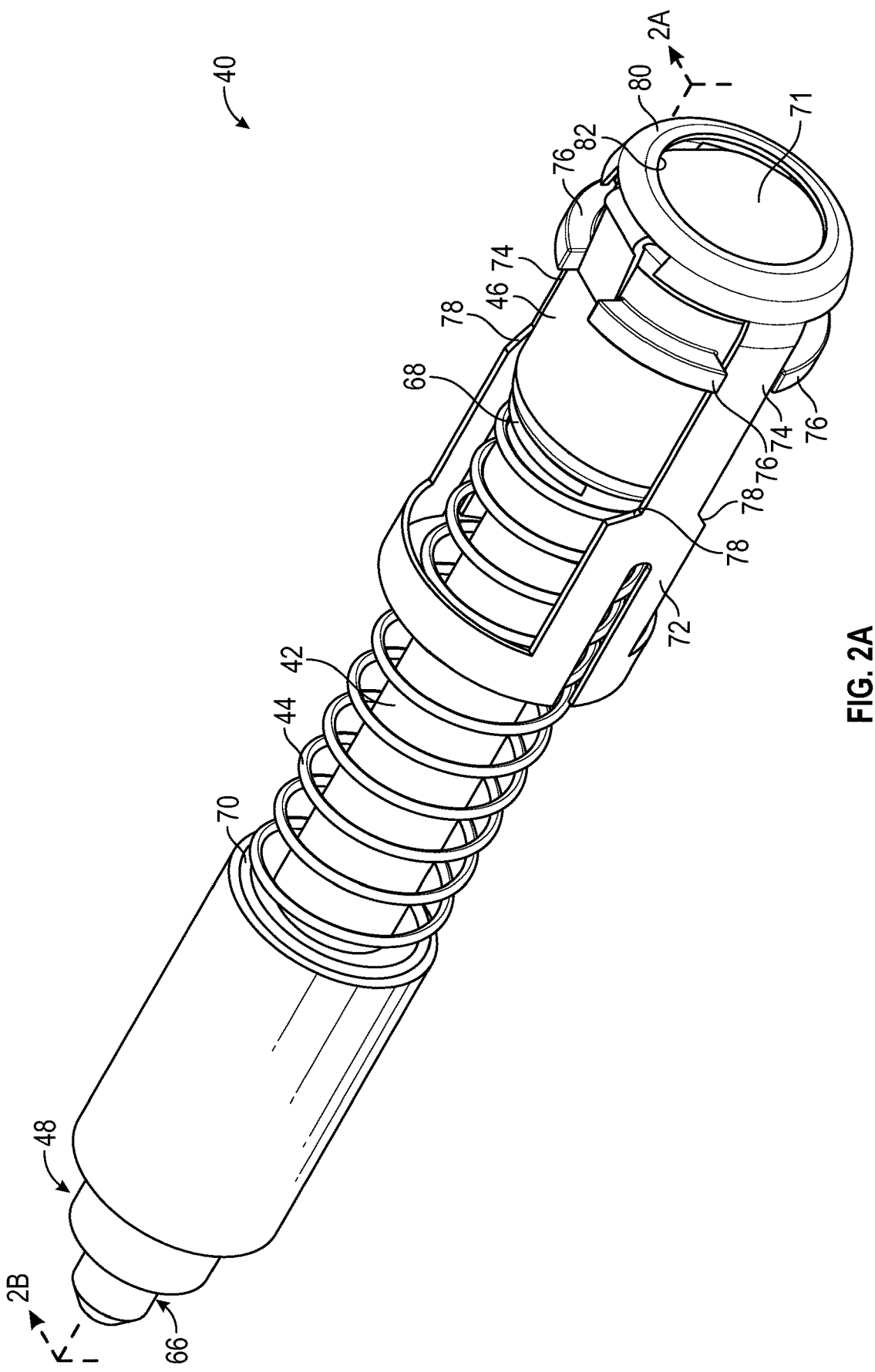
FIG. 2A is an upper perspective view of an example device to couple the catheter system to a medical device, illustrating an example housing of the device disposed in a proximal position, according to some embodiments.
Figure 2B:
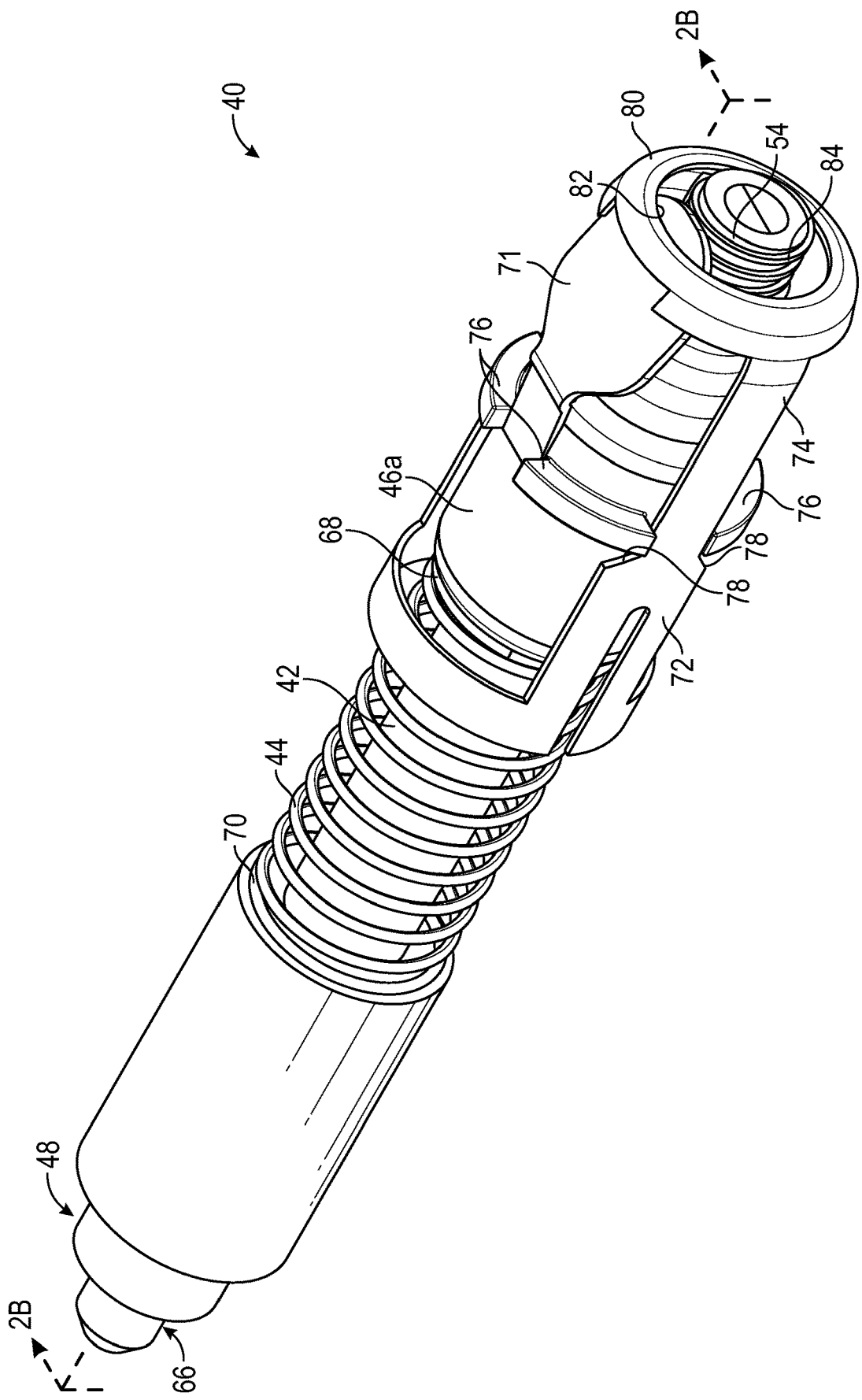
FIG. 2B is another upper perspective view of the device of FIG. 2A, illustrating the housing disposed in a first distal position, according to some embodiments.

In some embodiments, when the housing 46 is disposed in the proximal position, as illustrated, for example, in FIGS. 2A and 3A, the flap 71 may cover the connector 54, the antimicrobial compound 73 may contact the connector 54, and the spring 44 may be uncompressed. In some embodiments, the flap 71 may automatically swab the connector 54 in response to the flap 71 moving from a closed position, illustrated, for example, in FIG. 2A, to an open position, illustrated, for example, in FIG. 2B or FIG. 2C. In some embodiments, the antimicrobial compound 73 may be transferred from the flap 71 to the septum 56 in response to the flap 71 contacting and/or swabbing the septum 56.

In some embodiments, in response to movement of the housing 46 from the proximal position to the distal position, the spring 44 may be compressed and the flap 71 may open. In some embodiments, the distal position may include a first distal position, illustrated, for example, in FIGS. 2B and 3B or a second distal position, illustrated, for example, in FIGS. 2C and 3C.

In some embodiments, the device 40 may include a support structure 72, which may include one or more elongated guides 74. In some embodiments, the housing 46 may include one or more flanges 76. In some embodiments, in response to movement of the housing 46 from the proximal position to the distal position, the flanges 76 may be configured to move along the elongated guides 74 in a distal direction.

In some embodiments, the elongated guides 74 may include one or more stops 78. In some embodiments, the flanges 76 may be configured to move along the elongated guides 74 in the distal direction when the flanges 76 are proximal to and spaced apart from the stops 78. In some embodiments, in response to movement of the housing 46 in the distal direction and the flanges 76 contacting the stops 78, as illustrated, for example, in FIG. 2B, the housing 46 and the support structure 72 may be configured to move together in the distal direction. For example, in response to movement of the housing 46 in the distal direction and the flanges 76 contacting the stops 78, the housing 46 and the support structure 72 may be configured to move together in the distal direction from the position illustrated in FIG. 2B to the position in FIG. 2C. In some embodiments, the flanges 76 may facilitate holding or gripping of the housing 46 by the clinician.

In some embodiments, a proximal end 80 of the support structure 72 may include an opening 82. In some embodiments, a diameter of the opening 82 may be less than a diameter of the flap 71, which may prevent the flap 71 from opening and/or fully opening when the housing 46 is disposed in the proximal position.

Figure 2C:
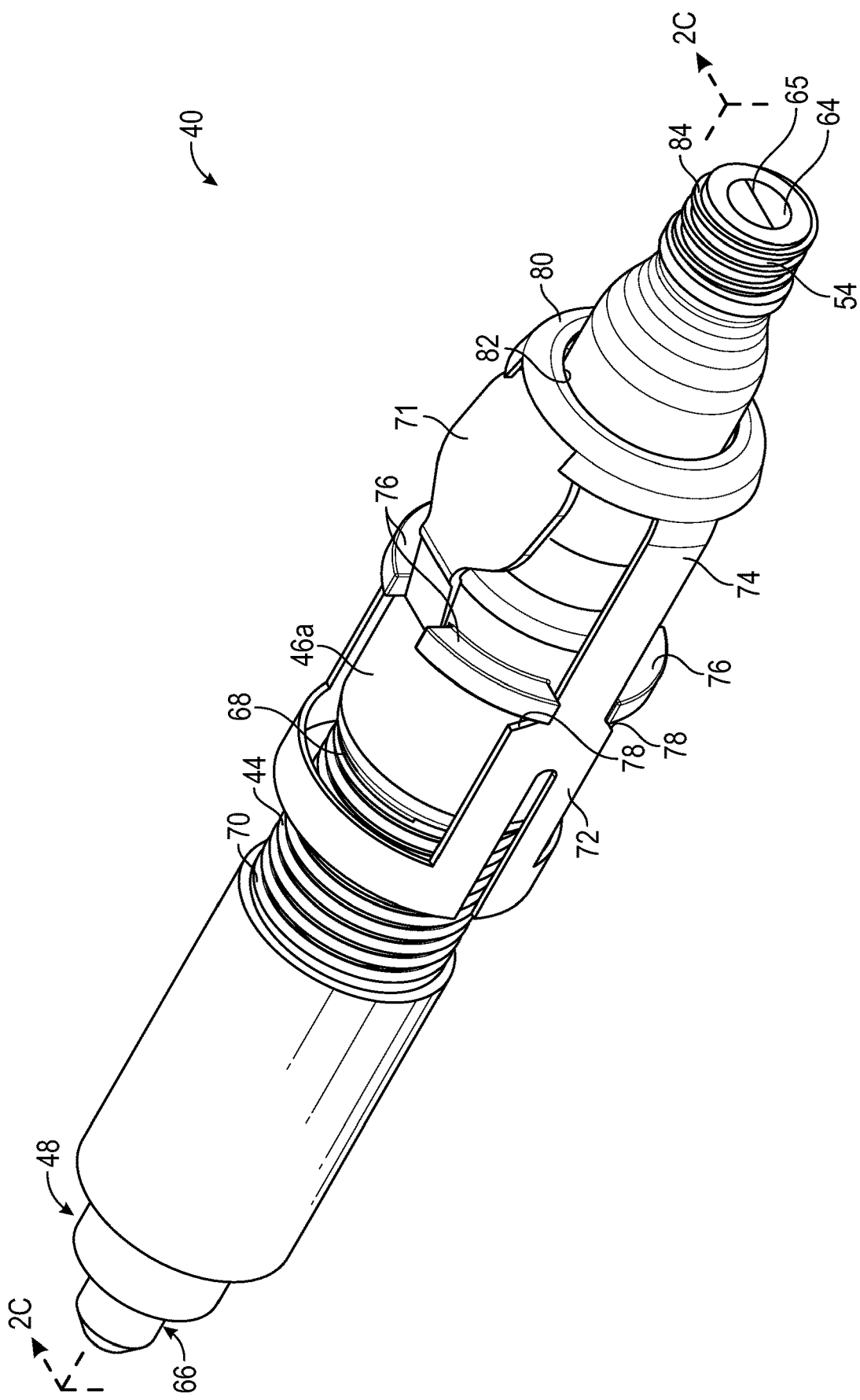
FIG. 2C is another upper perspective view of the device of FIG. 2A, illustrating the housing disposed in a second distal position, according to some embodiments.

In some embodiments, as illustrated in FIG. 2C and 3C, the connector 54 may be exposed for coupling to the access luer of the medical device. In some embodiments, threading 84 may be exposed, as illustrated in FIGS. 2C and 3C. In response to coupling of the access luer of the medical device to the connector 54, the flap 71 may be maintained in a fully open position, as illustrated, for example, in FIGS. 2C and 3C. In some embodiments, in response to the clinician releasing his or her hold on the housing 46 and/or the support structure 72, the spring 44 may return the housing 46 and/or the support structure 72 to the proximal position.

Referring now to FIGS. 4A-4E, in some embodiments, a housing 86 to disinfect a connector 88 may include a body 90, which may include a distal end 92, a proximal end 94, and a lumen 96 extending through the distal end 92 and the proximal end 94. In some embodiments, the distal end 92 may be configured to receive the connector 88. In some embodiments, the connector 88 may include or correspond to the connector 54 discussed with respect to FIGS. 2A-3C. In some embodiments, the proximal end 94 may include an access opening 98 configured to receive the medical device 102, such as an infusion device or syringe. In some embodiments, the housing 86 may be used with the catheter system 14 of FIG. 1 or any other suitable catheter system.

In some embodiments, the housing 86 may include a cover 100 coupled to the proximal end 94 of the body 90 and covering the access opening 98. In some embodiments, the cover 100 may include the antimicrobial compound 73. In some embodiments, in response to removal of the medical device 102 from the access opening 98, the cover 100 may be configured to automatically close, and the antimicrobial compound 73 may be configured to contact a proximal end of the connector 88. In some embodiments, the cover 100 may be spring-loaded, which may facilitate closing of the cover 100 in response to removal of the medical device 102 from the access opening 98. In some embodiments, the cover 100 may include a torsion spring. In some embodiments, the connector 88 may be enclosed or sealed within the housing 86 when the cover 100 is closed.

In some embodiments, the cover 100 may swab the connector 88 in response to the cover 100 moving from a closed position, illustrated, for example, in FIG. 4B, to an open position, illustrated, for example, in FIG. 4C. In some embodiments, the cover 100 may swab the connector 88 in response to the cover 100 moving from the open position to the closed position. In some embodiments, when the cover 100 is in the open position, the medical device 102 may be connected to the connector 88. In some embodiments, the automatic closing of the cover 100 and swabbing of the connector 88 in response to removal of the medical device 102 from the access opening 98 may protect the connector 88 from contamination by bacteria.

In some embodiments, the cover 100 may be coupled to the proximal end 94 at a pivot 104. In some embodiments, the cover 100 may be configured to pivot about the pivot 104 between the open position and the closed position. In some embodiments, the cover 100 may be configured to pivot about the pivot 104 on an axis generally parallel to a central axis 106 of the body 90. In some embodiments, the pivot 104 may include a pin or another suitable pivoting mechanism. In some embodiments, in response to opening of the cover 100, a new cleaning pad may be exposed and an old cleaning pad may be removed.

Referring now to FIGS. 5A-5E, in some embodiments, a housing 108 to disinfect the connector 88 may include a body 110, which may include a distal end 112, a proximal end 114, and a lumen 116 extending through the distal end 112 and the proximal end 114. In some embodiments, the distal end 112 may be configured to receive the connector 88. In some embodiments, the proximal end 114 may include an access opening 118 configured to receive the medical device 102, such as an infusion device or syringe. In some embodiments, the access opening 118 may be spaced apart from a proximal end 119 of the connector 88 such that the medical device 102 and the connector 88 may be directly coupled together. In some embodiments, the housing 108 may include or correspond to the housing 86 described with respect to FIGS. 4A-4E.

In some embodiments, the housing 108 may include a cover 120 coupled to the body 110 and covering the access opening 118. In some embodiments, the cover 120 may include the antimicrobial compound 73. In some embodiments, in response to removal of the medical device 102 from the access opening 118, the cover 120 may be configured to automatically close, and the antimicrobial compound 73 may be configured to contact the proximal end 119 of the connector 88. In some embodiments, the cover 120 may be spring-loaded, which may facilitate closing of the cover 120 in response to removal of the medical device 102 from the access opening 118. In some embodiments, the cover 120 may include a torsion spring. In some embodiments, the connector 88 may be enclosed or sealed within the housing 108 when the cover 120 is closed.

In some embodiments, the cover 120 may swab the connector 88 in response to the cover 120 moving from a closed position, illustrated, for example, in FIG. 5B, to an open position, illustrated, for example, in FIG. 5C. In some embodiments, the cover 120 may swab the connector 88 in response to the cover 120 moving from the open position to the closed position. In some embodiments, when the cover 120 is in the open position, the medical device 102 may be coupled to the connector 88. In some embodiments, the automatic closing of the cover 120 and swabbing of the connector 88 in response to removal of the medical device 102 from the access opening 118 may protect the connector 88 from contamination by bacteria.

In some embodiments, the cover 120 may be coupled to the body 110 at one or more pivots 122. In some embodiments, the cover 120 may be configured to pivot about the pivots 122 between the open position and the closed position. In some embodiments, the cover 120 may be configured to pivot about the pivots 122 between the open position and the closed position on an axis generally perpendicular to a central axis 124 of the body 110. In some embodiments, the pivots 122 may each include a pin or another suitable pivoting mechanism.

In some embodiments, a first distal arm 128a and a second distal arm 128b (which may be referred to collectively in the present disclosure as "distal arms 128") may extend from a first pivot 122a and a second pivot 122b (which may be referred to collectively in the present disclosure as "pivots 122"), respectively. In some embodiments, a first proximal arm 130a and a second proximal arm 130b (which may be referred to collectively in the present disclosure as "proximal arms 130") may be joined to the cover 120, which may be configured to contact the proximal end of the connector 88 when the cover 120 is in the closed position. In some embodiments, a semi-circular portion 132 may be disposed between the distal arms 128 and the proximal arms 130. In some embodiments, the semi-circular portion 132 may be configured to fit around the body 110 when the cover is in the open position such that the semi-circular portion and the body 110 contact each other and are not spaced apart.

Referring now to FIGS. 6A-6D, in some embodiments, a housing 134 to disinfect the connector 88 may include a body 136, which may include a distal end 138, a proximal end 140, and a lumen 142 extending through the distal end 138 and the proximal end 140. In some embodiments, the distal end 138 may be configured to receive the connector 88. In some embodiments, the proximal end 140 may include an access opening 144 configured to receive the medical device 102, such as an infusion device or syringe. In some embodiments, the access opening 144 may be spaced apart from a proximal end 119 of the connector 88 such that the medical device 102 and the connector 88 may be directly coupled together. In some embodiments, the housing 134 may include or correspond to the housing 86 described with respect to FIGS. 4A-4E and/or the housing 108 described with respect to FIG. 5A-5E.

In some embodiments, the housing 134 may include a cover 120 coupled to the body 136 and covering the access opening 144. In some embodiments, the cover 120 may include the antimicrobial compound 73. In some embodiments, in response to removal of the medical device 102 from the access opening 144, the cover 120 may be configured to automatically close, and the antimicrobial compound 73 may be configured to contact the proximal end 119 of the connector 88. In some embodiments, an antimicrobial strip (such as, for example, the antimicrobial strip 170 illustrated in FIGS. 7A-7D) may be disposed over the access opening 144. In some embodiments, the cover 120 may be spring-loaded, which may facilitate closing of the cover 120 in response to removal of the medical device 102 from the access opening 144. In some embodiments, the connector 88 may be enclosed or sealed within the housing 134 when the cover 120 is closed.

In some embodiments, the cover 120 may swab the connector 88 in response to the cover 120 moving from a closed position, illustrated, for example, in FIG. 6B, to an open position, illustrated, for example, in FIG. 6C. In some embodiments, the cover 120 may swab the connector 88 in response to the cover 120 moving from the open position to the closed position. In some embodiments, when the cover 120 is in the open position, the medical device 102 may be coupled to the connector 88. In some embodiments, the automatic closing of the cover 120 and swabbing of the connector 88 in response to removal of the medical device 102 from the access opening 144 may protect the connector 88 from contamination by bacteria.

In some embodiments, the cover 120 may be coupled to the body 136 at one or more pivots 148. In some embodiments, the cover 120 may be configured to pivot about the pivots 148 between the open position and the closed position. In some embodiments, the cover 120 may be configured to pivot about the pivots 148 between the open position and the closed position on an axis generally perpendicular to a central axis 149 of the body 136. In some embodiments, the pivots 148 may each include a pin or another suitable pivoting mechanism.

In some embodiments, the cover 120 may include a distal tab 150 and an L-shaped portion 152 coupled to the distal tab 150. In some embodiments, the pivots 148 may be disposed between the distal tab 150 and the L-shaped portion 152. In some embodiments, in response to depression of the distal tab 150, the L-shaped portion 152 may be raised and the access opening 144 may be exposed.

Referring now to FIGS. 7A-7D, in some embodiments, a housing 154 to disinfect the connector 88 may include a body 156, which may include a distal end 158, a proximal end 160, and a lumen 162 extending through the distal end 158 and the proximal end 160. In some embodiments, the housing 154 may include or correspond to one or more of the following: the housing 86 described with respect to FIGS. 4A-4E, the housing 108 described with respect to FIG. 5A-5E, and the housing 134 described with respect to FIGS. 6A-6D.

In some embodiments, the body 156 may include a distal piece 166 and a proximal piece 168, which may rotate with respect to the distal piece 166. In some embodiments, an antimicrobial strip 170 may be disposed over the access opening 164. In some embodiments, in response to rotation of the proximal piece 168 with respect to the distal piece 166, the antimicrobial strip 170 may advance and travel across the access opening 164 in a conveyor belt-like fashion. In some embodiments, the proximal piece 168 may be rotated in a first direction with respect to the distal piece 166, automatically pulling the antimicrobial strip 170 across the proximal end 119 of the connector 88 prior to use of the connector 88. In some embodiments, an aperture 172 in the antimicrobial strip 170 may allow the medical device 102 to access and couple to the connector 88.

In some embodiments, following uncoupling of the medical device 102 from the connector 88 and removal of the medical device 102 from the body 156, the proximal piece 168 may be rotated in the first direction to pull the antimicrobial strip 170 across the proximal end 119 and swab the proximal end 119 of the connector 88. In some embodiments, the antimicrobial strip 170 may include the antimicrobial compound 73. In some embodiments, a color change in the antimicrobial strip 170 may indicate the antimicrobial strip 170 is exhausted and the housing 154 may be replaced.

In some embodiments, rotating the distal piece 166 and/or the proximal piece 168 may turn a set of gears that translate the rotating motion into movement of the antimicrobial strip 170 across the aperture 172, allowing a fresh portion of the antimicrobial strip 170 to be exposed. In some embodiments, the set of gears may be part of a differential mechanism, which may include a crown wheel, pinion, sun gear, planetary gears, differential shaft, etc. as are understood in the art. In some embodiments, in response to the distal piece 166 and/or the proximal piece 168 being rotated in a first direction, the antimicrobial strip 170 may move across the aperture 172.

Referring now to FIGS. 8A-8G, in some embodiments, a device 174 to disinfect the connector 88 may include an inner housing 176, which may be annular, and an outer housing 178, which may be annular. In some embodiments, the inner housing 176 may include a proximal opening 179 and may be configured to receive the connector 88. In some embodiments, the connector 88 may be disposed in a snap fit with the inner housing 176. In some embodiments, the outer housing 178 may be moveable with respect to the inner housing 176 between a proximal position, illustrated, for example, in FIGS. 8A and 8C, and a distal position, illustrated, for example, in FIG. 8B. In some embodiments, the outer housing 178 may include a set of teeth 180.

In some embodiments, the device 174 may include a rachet wheel 182, which may include an inner set of teeth 184 and an outer set of teeth 186. In some embodiments, a first mandrel 188 may extend through the rachet wheel 182 and may include a pawl 190. In some embodiments, a second mandrel 192 may be disposed on an opposite side of the inner housing 176 as the first mandrel 188.

In some embodiments, an antimicrobial strip 194 may be wrapped around the second mandrel 192 and coupled to the first mandrel 188. In some embodiments, the antimicrobial strip 194 may extend over the proximal opening 179 of the inner housing 176. In some embodiments, in response to movement of the outer housing 178 between the proximal position and the distal position, the pawl 190 may catch against the inner set of teeth 184, the set of teeth 180 of the inner surface may successively engage the outer set of teeth 186, and the rachet wheel 182 and the first mandrel 188 may rotate such that the antimicrobial strip 194 moves across the proximal opening 179 of the inner housing 176. In some embodiments, the antimicrobial strip 194 may include cloth, tape, or another suitable material. In some embodiments, the antimicrobial strip 194 may include the antimicrobial compound 73.

In some embodiments, in response to movement of the outer housing 178 between the proximal position and the distal position, the antimicrobial strip 194 may wrapped around the first mandrel 188 and/or unwrapped from the second mandrel 192. In some embodiments, the antimicrobial strip 194 may include multiple holes 196 configured to allow the medical device 102 to extend through and couple to the connector 88 for infusion or blood withdrawal. In some embodiments, a distal end of the connector 88 may be coupled to extension tubing 34 or the adapter 38.

In some embodiments, the outer housing 178 may include a flap 198. In some embodiments, in response to movement of the outer housing 178 between the proximal position and the distal position, the flap 198 may be opened. In some embodiments, the outer housing 178 may be configured to enclose the connector 88.

In some embodiments, the device 174 may include another rachet wheel 200, which may also include the inner set of teeth 184 and the outer set of teeth 186. In some embodiments, the first mandrel 188 may extend through the other rachet wheel 200. In some embodiments, the antimicrobial strip 194 may be disposed between the rachet wheel 182 and the other rachet wheel 200. In some embodiments, the device 174 may include an arm 202 extending through the first mandrel 188. In some embodiments, the first mandrel 188 may be configured to rotate with respect to the arm 202. In some embodiments, the arm 202 may be coupled to the inner housing 176.

Figure 9A:
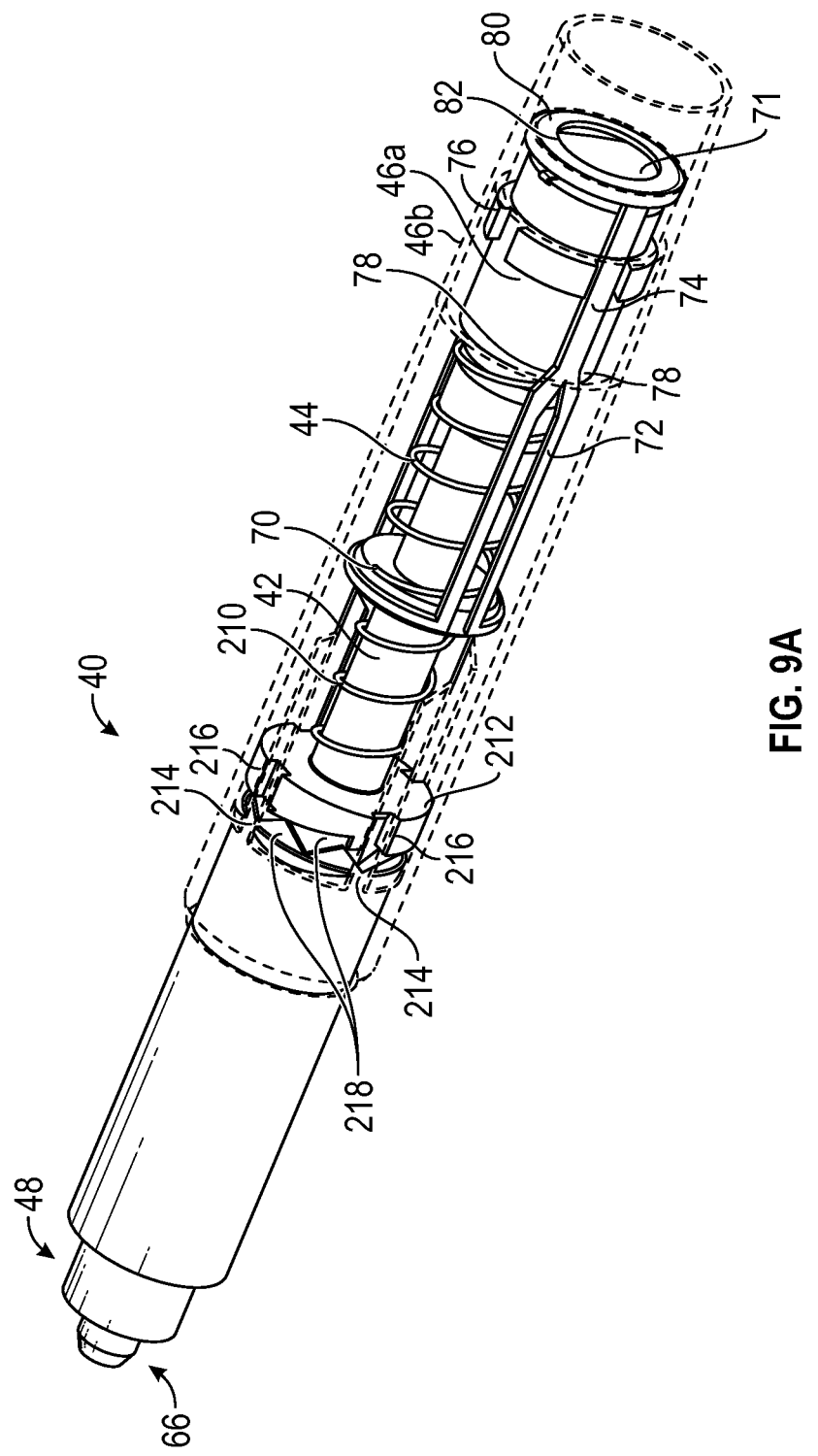
FIG. 9A is an upper perspective view of the device of FIG. 2A, illustrating the device in a retracted position, according to some embodiments.

Referring now to FIG. 9A, the device 40 is illustrated in a retracted position, according to some embodiments. In some embodiments, when the device 40 is in the retracted position, the housing 46 may be in the proximal position. In some embodiments, the housing 46 and the body 42 may be configured to slide axially towards each other to move the device 40 from the retracted position in which the connector 54 is enclosed in the housing 46 to a projected position in which the connector 54 is exposed proximal to the housing. For example, the housing 46 may slide axially in a distal direction from the retracted position and/or the body 42 may slide axially in a proximal direction from the retracted position. In some embodiments, the housing 46 may slide axially in the distal direction to open the flap 71, and after the flap 71 is open, the connector 54 may move proximally and outside the housing 46. In some embodiments, when the device 40 is in the projected position, the housing 46 may be disposed in the distal position.

In some embodiments, the device 40 may include a spring 210, which may include a proximal end and a distal end. In some embodiments, the proximal end of the spring 210 may be coupled to the body 42. In some embodiments, the distal end of the spring 210 may urge a cam body 212 of the device 40 distally. In some embodiments, an inner surface of the outer portion 46b may include one or more rails 214. In some embodiments, an outer surface of the cam body 212 may include one or more slots 216, which may extend completely or partially through the cam body 212. In some embodiments, when the device 40 is in the retracted position, as illustrated, in FIG. 9A, the rails 214 may be disposed within the slots 216, which may prevent rotation of the cam body 212.

Figure 9B:
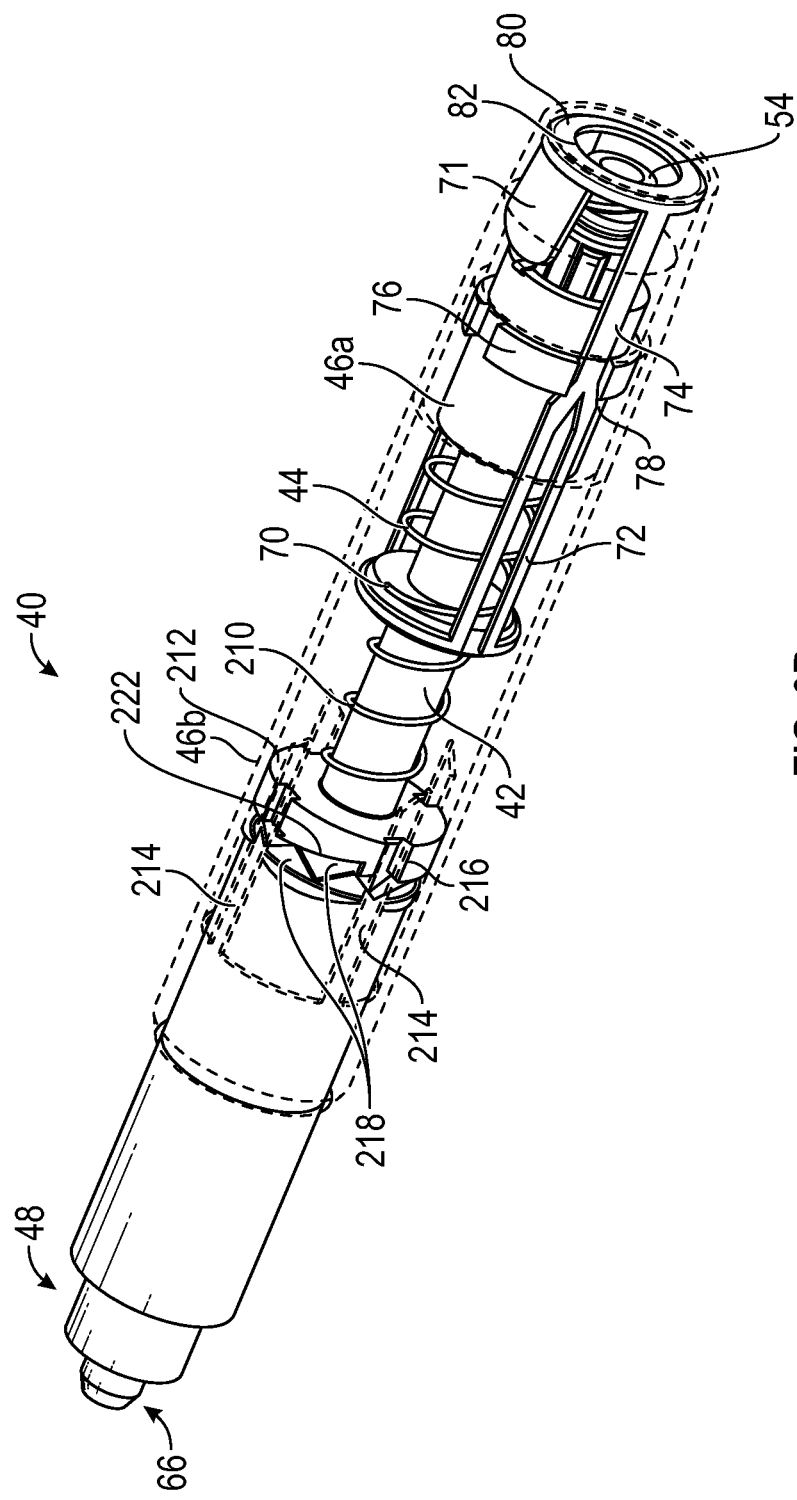
FIG. 9B is an upper perspective view of the device of FIG. 2A, illustrating the housing and the body sliding axially toward each other to move the device from the retracted position to a projected position, according to some embodiments.

Referring now to FIG. 9B, in some embodiments, as the device 40 moves from the retracted position to the projected position, the body 42 may slide axially in the proximal direction and/or the housing 46 may slide axially in the distal direction. In these embodiments, the rails 214 may slide within the slots 216. In some embodiments, as the housing 46 slides axially in the distal direction, the flanges 76 may move along the elongated guides 74 or the flanges 76 and the support structure 72 may move together in the distal direction.

Figure 9C:
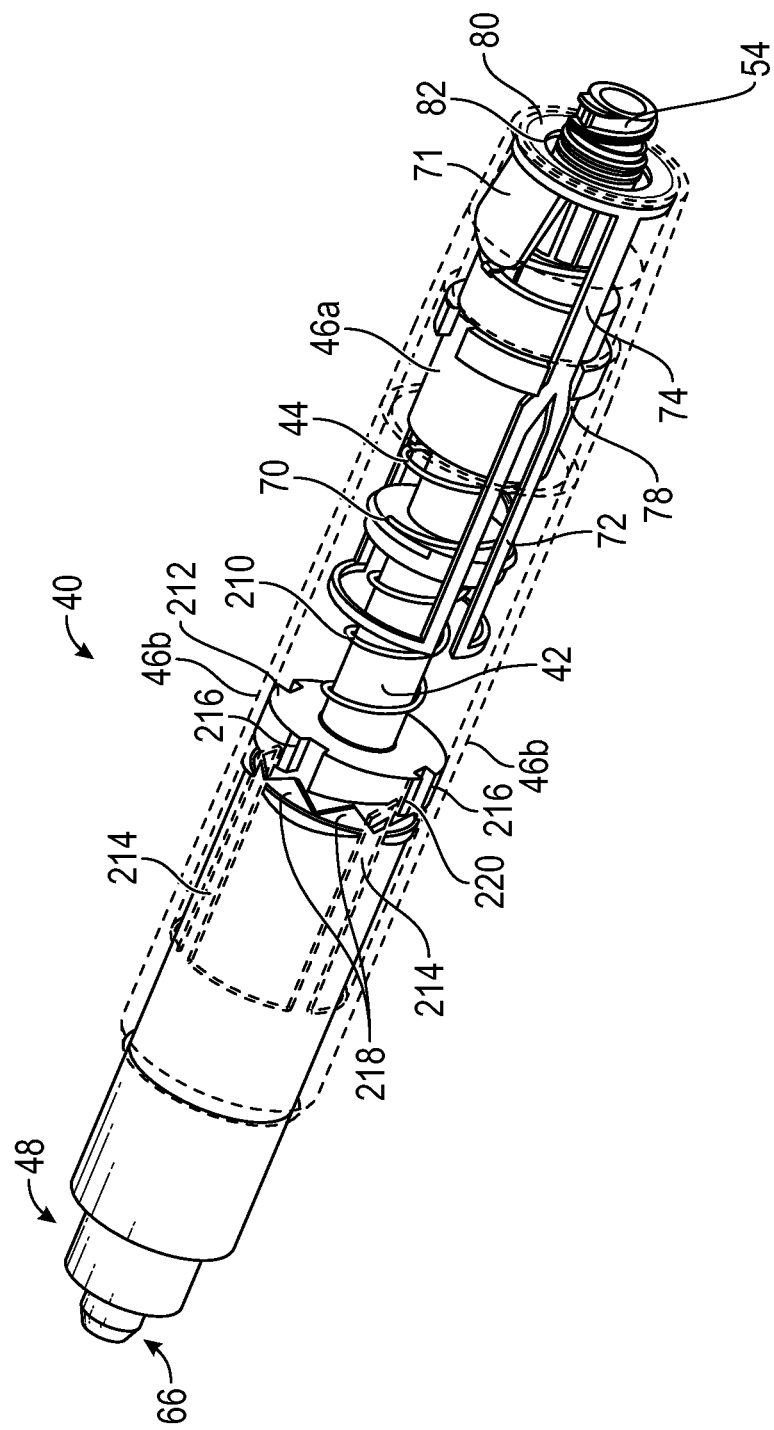
FIG. 9C is an upper perspective view of the device of FIG. 2A, illustrating the device in the projected position, according to some embodiments.

Referring now to FIG. 9C-9E, the device 40 is illustrated in the projected position, according to some embodiments. In some embodiments, in response to the housing 46 and the body 42 sliding axially towards each other, the rails 214 may be removed from the slots 216, which may allow the cam body 212 to rotate. In some embodiments, one or more angled surfaces of the cam body 212 and/or one or more teeth 218 coupled to the body 42 may cause the cam body 212, which may be urged distally by the spring 210, to rotate. In some embodiments, the cam body 212 may rotate until the rails 214 contact a stop surface 220 of the cam body 212, as illustrated, for example, in FIG. 9C.

In some embodiments, the device 40 may be locked in the projected position. In some embodiments, the rails 214 and/or the teeth 218 may contact the cam body 212 when the device 40 is in the projected position, which may lock the device 40 in the projected position. In some embodiments, in response movement of the body 42 proximally beyond the projected position, the device 40 may be configured to unlock and return to the retracted position. For example, the rails 214 may no longer contact the stop surface 220 and the cam body 212 may rotate such that the rails 214 can slide through the slots 216.

Figure 9F:
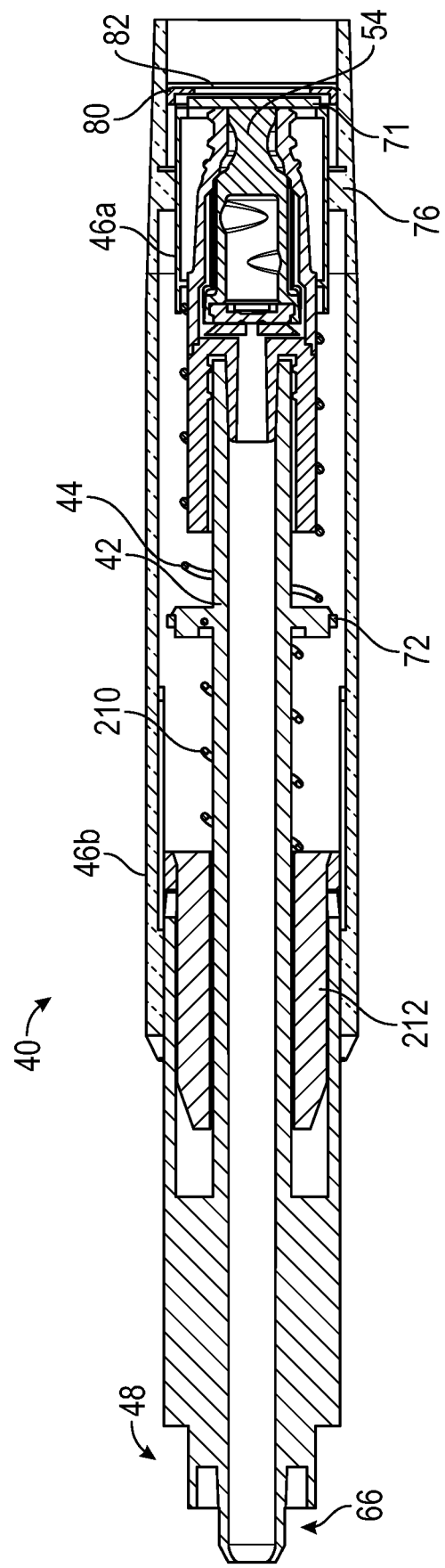
FIG. 9F is a cross-sectional view of the device of FIG. 2A, illustrating the device in the retracted position, according to some embodiments.

Referring now to FIG. 9F, in some embodiments, when the device 40 is in the retracted position, the flap 71 may cover the connector 54 and/or the antimicrobial compound 73 may contact the connector 54. In some embodiments, the flap 71 may automatically swab the connector 54 in response to the flap 71 moving from a closed position, illustrated, for example, in FIG. 9F, to an open position, illustrated, for example, in FIGS. 9C-9E. In some embodiments, the antimicrobial compound 73 may be transferred from the flap 71 to the septum 56 in response to the flap 71 contacting and/or swabbing the septum 56.

Figure 10A:
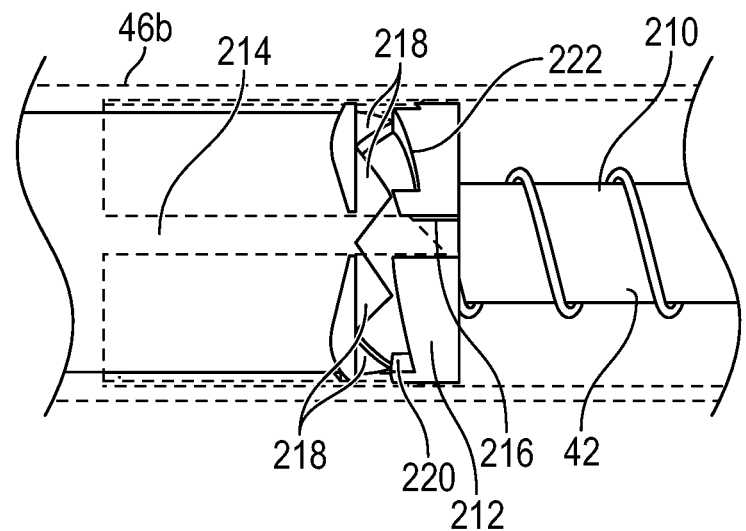
FIG. 10A is an enlarged upper perspective view of a portion of the device of FIG. 2A, illustrating the housing and the body in a first position, according to some embodiments.

Referring now to FIGS. 10A-10G, a sequence of positions of the device 40 is illustrated in order from 10A-10G, according to some embodiments. As illustrated in FIG. 10A, in some embodiments, in response to the housing 46 and the body 42 sliding axially towards each other to a first position, the rails 214 may partially be removed from the slots 216.

Figure 10B:
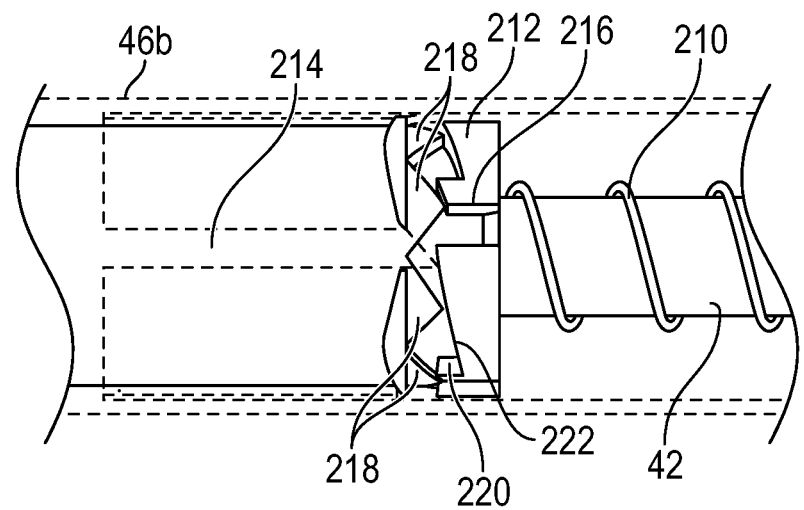
FIG. 10B is an enlarged upper perspective view of the portion of the device of FIG. 2A, illustrating the housing and the body in a second position, according to some embodiments.

As illustrated in FIG. 10B, in some embodiments, in response to the housing 46 and the body 42 sliding axially towards each other to a second position, the rails 214 may be removed from the slots 216, which may allow the cam body 212 to rotate. In some embodiments, the angled surfaces 222 of the cam body 212 and/or one or more teeth 218 coupled to the body 42 may cause the cam body 212, which may be urged distally by the spring 210, to rotate.

Figure 10C:
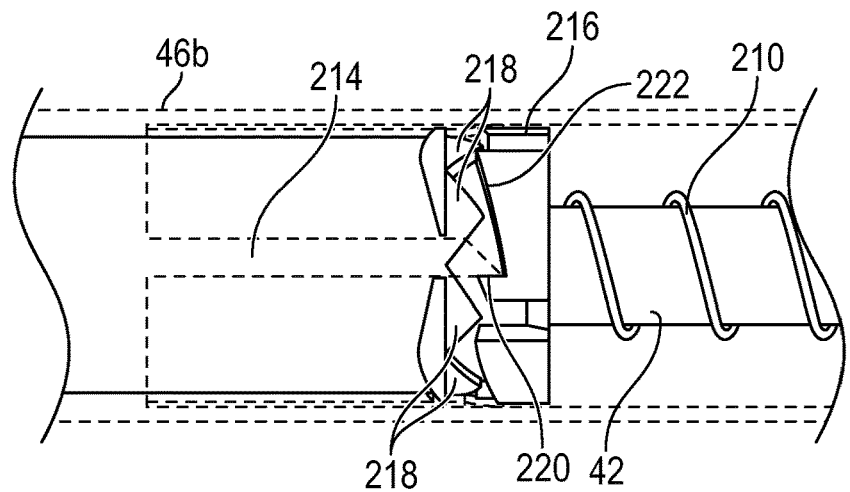
FIG. 10C is an enlarged upper perspective view of the portion of the device of FIG. 2A, illustrating the device locked in the projected position.

As illustrated in FIG. 10C, in some embodiments, the cam body 212 may rotate until the rails 214 contact the stop surface 220 of the cam body 212. In some embodiments, the rails 214 and/or the teeth 218 may contact the cam body 212 when the device 40 is in the projected position, which may lock the device 40 in the projected position.

Figure 10D:
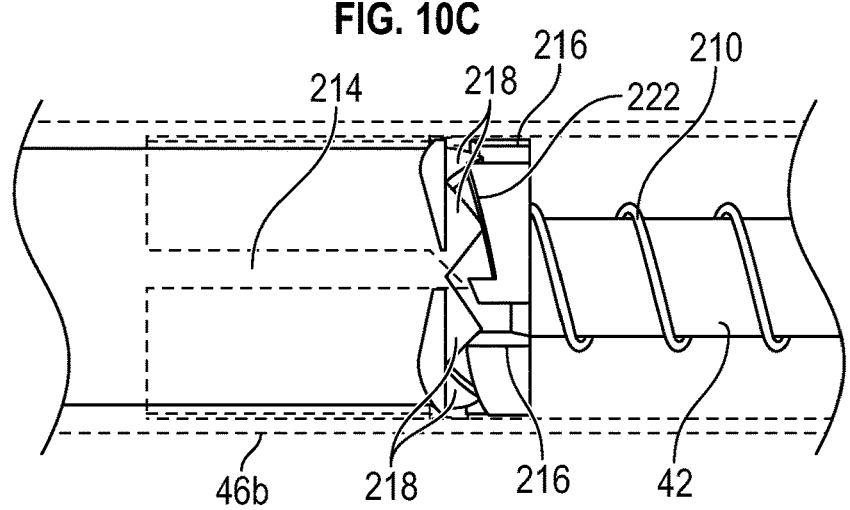
FIG. 10D is an enlarged upper perspective view of the portion of the device of FIG. 2A, illustrating the housing and the body in a third position, according to some embodiments.
Figure 10E:
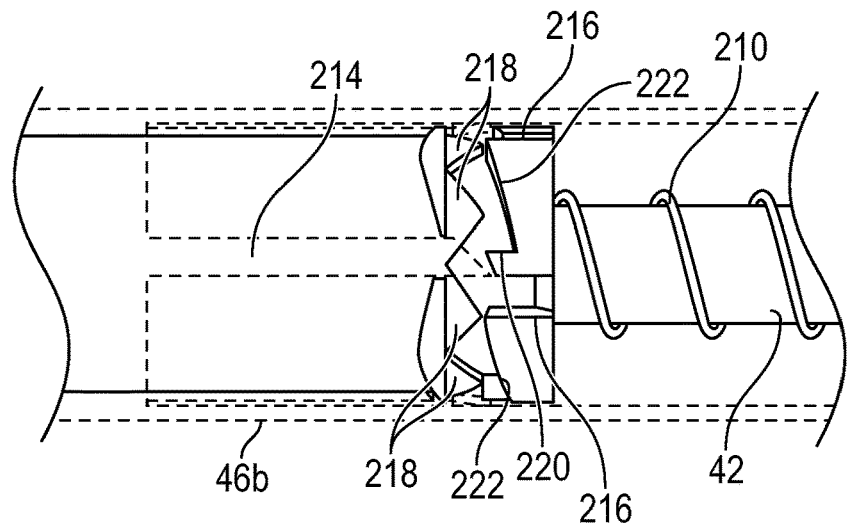
FIG. 10E is an enlarged upper perspective view of the portion of the device of FIG. 2A, illustrating the housing and the body in a fourth position, according to some embodiments.
Figure 10F:
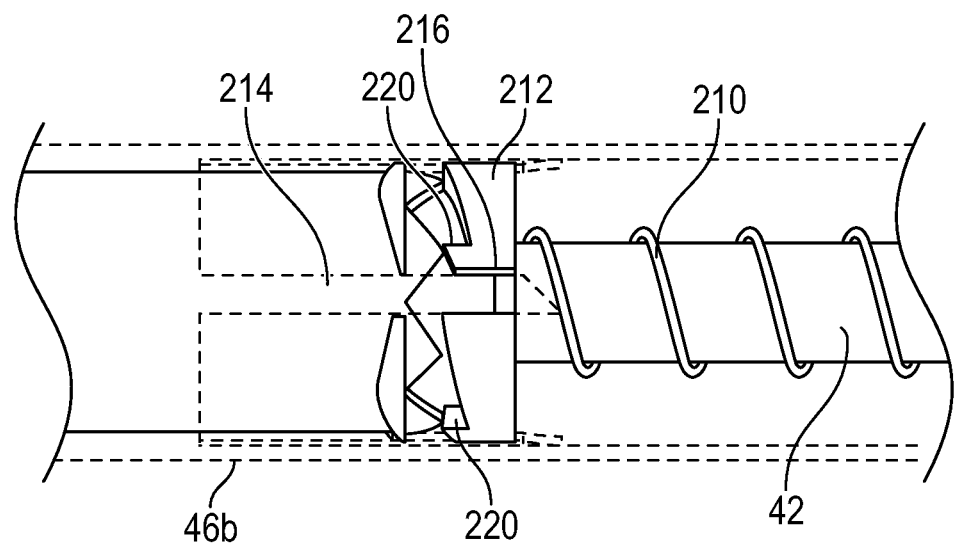
FIG. 10F is an enlarged upper perspective view of the portion of the device of FIG. 2A, illustrating the housing and the body in a fifth position, according to some embodiments.
Figure 10G:
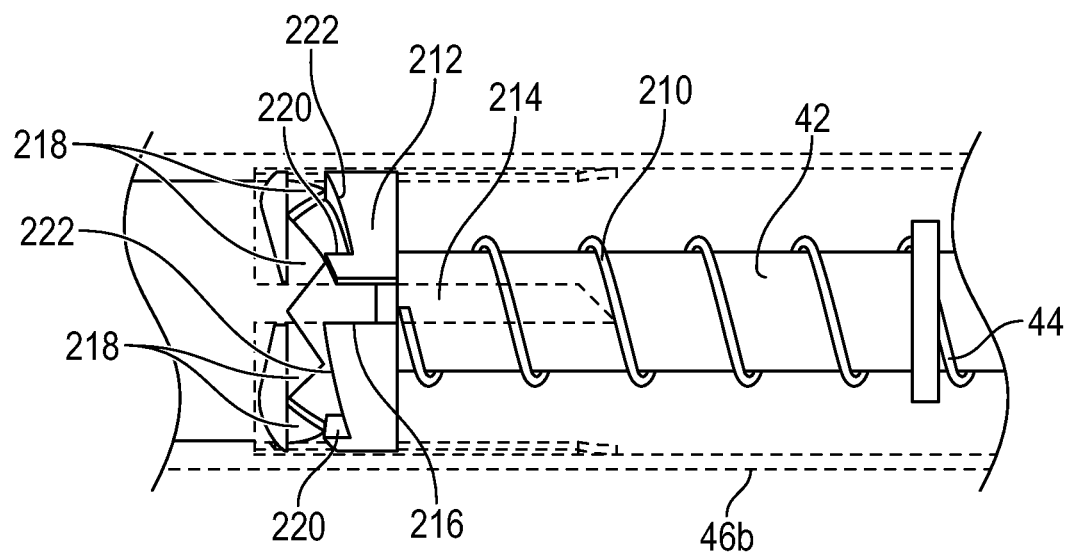
FIG. 10G is an enlarged upper perspective view of the portion of the device of FIG. 2A, illustrating the device in the retracted position, according to some embodiments.

As illustrated in FIGS. 10D-10E, in some embodiments, in response movement of the body 42 proximally beyond the projected position or the connector 54 moving further from the housing 46 than in the projected position, the device 40 may be configured to unlock and return to the retracted position. For example, the rails 214 may no longer contact the stop surface 220 and the cam body 212 may rotate such that the rails 214 can slide through the slots 216, as illustrated, for example, in FIGS. 10F-10G.

FIGS. 9-10 illustrate an example mechanism for moving the device 40 from the retracted position to the projected position and back to the retracted position, according to some embodiments. It is understood that variations of the mechanism or other mechanisms may be used. All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A device to couple a vascular access device to a medical device, the device comprising:
   a housing;
   a body partially disposed within the housing, wherein the body comprises a distal end, a proximal end, and a lumen extending through the distal end and the proximal end, wherein the proximal end comprises a connector,
   wherein the housing and the body are configured to slide axially towards each other to move the device from a retracted position in which the connector is enclosed within the housing to a projected position in which the connector is exposed proximal to the housing; and
   a spring, wherein the spring comprises a distal end and a proximal end, wherein the distal end of the spring is coupled to the body, wherein the proximal end of the spring urges the housing proximally.

2. The device of claim 1, wherein the housing comprises a flap, wherein when the device is in the retracted position, the flap covers the connector, wherein in response to the housing moving distally from the retracted position, the flap opens.

3. The device of claim 2, wherein the flap comprises an antimicrobial compound, wherein when the device is in the retracted position, the antimicrobial compound contacts the connector.

4. The device of claim 1, wherein the distal end of the body comprises a luer connector.

5. The device of claim 1, further comprising a support structure comprising an elongated guide, wherein the housing comprises a flange, wherein in response to movement of the housing from distally from the retracted position, the flange is configured to move along the elongated guide in a distal direction.

6. The device of claim 5, wherein the elongated guide comprises a stop, wherein the flange is configured to move along the guide in the distal direction when the flange is proximal to and spaced apart from the stop, wherein in response to movement of the housing in the distal direction from the retracted position and the flange contacting the stop, the housing and the support structure are configured to move together in the distal direction.

7. The device of claim 1, wherein the device is configured to lock in the projected position.

8. The device of claim 7, wherein in response movement of the body proximally beyond the projected position, the device is configured to unlock and return to the retracted position.

9. A device to couple a vascular access device to a medical device, the device comprising:
   a housing;
   a body partially disposed within the housing, wherein the body comprises a distal end, a proximal end, and a lumen extending through the distal end and the proximal end, wherein the proximal end comprises a connector,
   wherein the housing and the body are configured to slide axially towards each other to move the device from a retracted position in which the connector is enclosed within the housing to a projected position in which the connector is exposed proximal to the housing; and
   a support structure comprising an elongated guide, wherein the housing comprises a flange, wherein in response to movement of the housing from distally from the retracted position, the flange is configured to move along the elongated guide in a distal direction.

10. The device of claim 9, wherein the elongated guide comprises a stop, wherein the flange is configured to move along the guide in the distal direction when the flange is proximal to and spaced apart from the stop, wherein in response to movement of the housing in the distal direction from the retracted position and the flange contacting the stop, the housing and the support structure are configured to move together in the distal direction.

11. The device of claim 9, wherein the housing comprises a flap, wherein when the device is in the retracted position, the flap covers the connector, wherein in response to the housing moving distally from the retracted position, the flap opens.

12. The device of claim 9, further comprising a spring, wherein the spring comprises a distal end and a proximal end, wherein the distal end of the spring is coupled to the body, wherein the proximal end of the spring urges the housing proximally.

13. The device of claim 9, wherein the flap comprises an antimicrobial compound, wherein when the device is in the retracted position, the antimicrobial compound contacts the connector.

14. The device of claim 9, wherein the distal end of the body comprises a luer connector.

15. The device of claim 9, wherein the device is configured to lock in the projected position.

16. The device of claim 15, wherein in response movement of the body proximally beyond the projected position, the device is configured to unlock and return to the retracted position.

* * * * *